(12) United States Patent
Van De Maele

(10) Patent No.: US 9,603,750 B2
(45) Date of Patent: Mar. 28, 2017

(54) METHOD AND APPARATUS FOR PRODUCING COMPOSITE STRUCTURE

(75) Inventor: Marleen Van De Maele, Buggenhout (BE)

(73) Assignee: ROMANOVA BVBA STARTER, Buggenhout (BE)

( * ) Notice: Subject to any disclaimer, the term of this patent is extended or adjusted under 35 U.S.C. 154(b) by 526 days.

(21) Appl. No.: 13/879,498

(22) PCT Filed: Oct. 13, 2011

(86) PCT No.: PCT/EP2011/005138
§ 371 (c)(1),
(2), (4) Date: Oct. 22, 2013

(87) PCT Pub. No.: WO2012/048878
PCT Pub. Date: Apr. 19, 2012

(65) Prior Publication Data
US 2014/0039437 A1 Feb. 6, 2014

(30) Foreign Application Priority Data

Oct. 13, 2010 (EP) .................................... 10447020
Oct. 13, 2010 (EP) .................................... 10447021
(Continued)

(51) Int. Cl.
*A61F 13/532* (2006.01)
*B32B 5/30* (2006.01)
(Continued)

(52) U.S. Cl.
CPC .. *A61F 13/15585* (2013.01); *A61F 13/15658* (2013.01); *A61F 13/539* (2013.01);
(Continued)

(58) Field of Classification Search
CPC ............ A61F 13/15658; A61F 13/5323; A61F 2013/15861; A61F 2013/15869;
(Continued)

(56) References Cited

U.S. PATENT DOCUMENTS 4,209,553 A * 6/1980 Greenberg ......... D06B 11/0066
118/301
4,715,918 A * 12/1987 Lang ................. A61F 13/15634
156/273.1
(Continued)

FOREIGN PATENT DOCUMENTS

EP 0432126 A1 4/1990
EP 1142785 A1 10/2001
(Continued)

*Primary Examiner* — Michael Tolin
(74) *Attorney, Agent, or Firm* — Dennemeyer & Associates, LLC

(57) ABSTRACT

The present invention relates to a method and apparatus for forming a composite structure, preferably for use in an absorbent structure used within the personal hygiene industry, such as for instance feminine hygiene garments, baby diapers and pants and adult incontinence garments. The present invention preferably provides a method and apparatus for depositing and positioning particulate materials in a desired pattern onto a moving carrier layer. The method allows accurate forming of a pattern of particulate material clusters at high production speed having improved attachment properties, with reduced raw material usage and relative low cost. The present invention foresees in the need for improved thin, flexible, lightweight absorbent structure having optimal absorption, distribution and retention.

6 Claims, 10 Drawing Sheets

(30) Foreign Application Priority Data

| Oct. 13, 2010 | (EP) | 10447022 |
|---|---|---|
| Oct. 13, 2010 | (EP) | 10447023 |
| Oct. 13, 2010 | (EP) | 10447024 |
| Feb. 3, 2011 | (EP) | 111532685 |

(51) Int. Cl.
*B32B 37/24* (2006.01)
*B05C 1/10* (2006.01)
*B05D 1/32* (2006.01)
*A61F 13/15* (2006.01)
*B05C 19/04* (2006.01)
*A61F 13/539* (2006.01)
*B32B 3/28* (2006.01)
*B32B 5/16* (2006.01)
*B32B 37/00* (2006.01)
*D04H 1/46* (2012.01)
*A61F 13/53* (2006.01)

(52) U.S. Cl.
CPC ............ *A61F 13/5323* (2013.01); *B05C 1/10* (2013.01); *B05C 19/04* (2013.01); *B05D 1/32* (2013.01); *B32B 3/28* (2013.01); *B32B 5/16* (2013.01); *B32B 5/30* (2013.01); *B32B 37/0076* (2013.01); *B32B 37/24* (2013.01); *D04H 1/465* (2013.01); *A61F 2013/530562* (2013.01); *A61F 2013/530591* (2013.01); *B05D 2401/32* (2013.01); *B32B 2555/02* (2013.01); *Y10T 428/239* (2015.01); *Y10T 428/24893* (2015.01)

(58) Field of Classification Search
CPC .......... A61F 2013/53051; A61F 2013/530562; A61F 2013/530591; B32B 5/30; B32B 37/24; B32B 2555/02; B32B 5/15; B05C 1/10; B05C 19/04; B05D 1/32; B05D 2401/32

See application file for complete search history.

(56) References Cited

U.S. PATENT DOCUMENTS

| 5,118,376 | A | * | 6/1992 | Pigneul | A61F 13/15658 |
|---|---|---|---|---|---|
| | | | | | 156/219 |
| 6,591,584 | B1 | * | 7/2003 | Saito | 53/450 |
| 6,833,014 | B2 | * | 12/2004 | Welygan | B24D 3/002 |
| | | | | | 51/293 |
| 2006/0021695 | A1 | * | 2/2006 | Blessing | A61F 13/15658 |
| | | | | | 156/196 |
| 2007/0167928 | A1 | | 7/2007 | Becker et al. | |
| 2008/0312621 | A1 | | 12/2008 | Humdorf et al. | |
| 2014/0296817 | A1 | * | 10/2014 | Van Malderen | A61F 13/15658 |
| | | | | | 604/385.01 |

FOREIGN PATENT DOCUMENTS

| EP | 1621166 | | 2/2006 |
|---|---|---|---|
| EP | 1632206 | A1 | 8/2006 |
| EP | 1655007 | A1 | 10/2006 |
| GB | 2283680 | A | 5/1995 |
| JP | 2006-263074 | A | 10/2006 |
| WO | 95/21596 | A1 | 8/1995 |

* cited by examiner

METHOD AND APPARATUS FOR PRODUCING COMPOSITE STRUCTURE

FIELD OF THE INVENTION

The present invention relates to a method and apparatus for depositing particulate material in a desired pattern onto a moving carrier layer. The method allows accurate forming of a predetermined pattern of particulate material clusters at high production speed and relative low cost. Such method is particularly useful in the manufacture of absorbent composites for use in absorbent structure of absorbent article, preferably a disposable article, such as a feminine hygiene garment, baby diaper, baby pants and adult incontinence garment.

BACKGROUND OF THE INVENTION

Disposable absorbent articles have an absorbent structure for absorbing bodily exudates, a soft liquid-permeable top sheet on the wearer side and a liquid-impermeable back sheet on the garment side. The absorbent structure in between is normally made from a mixture of cellulose fibers or other fibrous substance and an absorbent polymer material. These fibrous substances make these absorbent articles typically quite fluffy and bulky.

In recent years there has been increasing demand for flexible, thinner, lightweight absorbent structures to resolve various problems of manufacturing, marketing, design, fit, wearing comfort, distribution, garbage disposal, material and energy consumption, transportation and storage costs and the like.

The most common method currently used to meet these demands in disposable absorbent articles is to reduce the amount of cellulose fibre or other support material within and surrounding the absorbent structure and/or use larger amounts of absorbent polymer materials. Consequently such absorbent articles have a smaller proportion of hydrophilic cellulose fibres and/or a higher proportion of absorbent polymers materials. Some of these absorbent articles may be better at storing liquid, however they are not necessarily good at absorbing and distributing liquid when the absorbent article is actually being used. It will thus be apparent from the above that the absolute and relative proportions of the fibrous material and absorbent polymer material are closely linked in light of article performance. Hence there are limits on reducing the amount of hydrophilic cellulose fibre and reducing the thickness of absorbent cores.

Many attempts have been undertaken to manufacture flexible, thin, lightweight absorbent structures, consisting of a high amount of absorbent polymer material. In order to obtain good absorbency, distribution and retention within such absorbent structures it has found to be important to at least partially immobilize the absorbent material. Failing to provide sufficient structural integrity results in loss of functional performance characteristics such as coherence, absorption, distribution and/or retention and results in failures related but not limited to for instance leakages, high rewet values, etc. On the other hand however the presence of this physical and/or chemical interaction in between the absorbent material and the restraining material often also leads to a reduced absorption, distribution and/or retention performance. This is especially the case when such flexible, thin, lightweight absorbent structures, consisting of an absorbent polymer material are placed in between multiple enveloping layers.

The larger proportion of absorbent polymer materials and related immobilisation requirements in substantially cellulose free absorbent articles may thus greatly inhibit the absorption, distribution and/or retention of liquids if inadequately managed. It will be clear that the absolute and relative proportions of the hydrophilic cellulose fibres and absorbent polymer materials need to be tightly controlled in order to maintain the absorbent properties of the absorbent structures. Certainly decreased absorption speed and fluid distribution are common causes of failure. Since such hygienic absorbent articles are generally also disposable and need in some instances to be worn over many hours they require performance in a dry state as well as in a partially and fully bodily exudates loaded state.

The ability and capacity of an absorbent polymer material to absorb, distribute and retain liquid is dependent upon the form, position and/or manner in which the absorbent polymer material is incorporated into the absorbent structure. Since many absorbent structures have a relatively homogeneous and continuous distribution of absorbent polymer material, and thus exhibit a substantial homogeneous swelling, for second, third and next liquid insults such absorbent layers may actually act as a liquid barrier. This gel-blocking occurs when the absorbent polymer material located in regions of first contact starts to increase in volume as a consequence of imbibing the fluid, thereby forming a hydrogel. Gel blocking in and adjacent a zone of the absorbent layer of initial liquid contact prevents liquid from rapidly dispersing or wicking past the "blocking" material into the rest of the absorbent layer and further liquid uptake by the absorbent layer must then take place via for instance a diffusion process that is much slower than the rate at which liquid is applied to the absorbent layer. Especially when absorbent polymer material concentrations are absolutely or relatively high and wetted, the hydro-gel can block the initial and/or additional fluid from reaching other still more absorbent regions of the absorbent core, thus leading to unappreciated, underused or unused absorbent capacity. The diminished capacity results in leakages, well before the absorbent core is fully saturated.

Gel-blocking is even increased in thin substantially cellulose free structures where the liquid find little or limited macroscopic voids and/or spaces which can be used for temporary, intermediate or final liquid storage. Also the structural volume restrictions of these absorbent structures lead to a further reduced absorbent performance due to limited swelling capacity of the absorbent polymer material increasing the tendency to functional failures and leakages. To remedy, absorbent article designers have and typically use additional side cuffs and acquisition layers which are expensive, inefficient and can only partly remedy these limitations. By not completely abandoning the use of hydrophilic fibrous materials next to the use of absorbent polymer materials this problem can be partially resolved, however, it will be clear that in such case the absolute and relative proportions of absorbent materials will unwillingly be restricted and thus any thickness reduction of the absorbent structure not fully optimised.

It has been found in order to be able to keep absorbent materials compartmentalized, restrained and/or bound within the absorbent structures during use, it is preferred to deposit such absorbent material in a predetermined and desired location, grids or pattern during the manufacturing process. It is therefore very desirable to enable the depositing of absorbent materials in a substantially continuously, specific, well-defined and discretely arranged pattern onto a carrier layer moving at a relatively high speed.

The present invention is not only useful for the hygiene industry (e.g. for feminine hygiene garments, baby diapers and baby pants, adult incontinence garments) but may find applications in a multitude of industries such as the food industry (e.g. for coffee pads), the consumer industry (e.g. for disposable body warmers), the household industry (e.g. sheet formed detergent articles), construction (e.g. filter materials and insulation) as well as many other areas where it is desirable to deposit and immobilise particle materials on to a high-speed carrier layer.

Multiple attempts have been made to provide methods to manufacture composite structures with selected regions of particulate materials intermittently and discretely located along the length of a carrier layer. U.S. Pat. No. 5,494,622 describes a process and apparatus for forming sandwich-like structures having clusters of absorbent particulate material which are in a pattern chamber directly drawn and deposited on to the surface of the carrier layer by gas flow facilitated vacuum means. Due to the fact the pattern chamber is in contact with several pocket regions at a time, the filling of the pockets often results in under- and/or overfilling during the forming process leading to inefficient use of raw materials and leading to under-performing absorbent structures, structural failures and leakages. EP1621166 describes a process and apparatus for forming a substantially cellulose free sandwich-like structure having pre-metered clusters of absorbent particulate material held in pre-arranged patterns before being discretely deposited onto the carrier layer so as to have the same pre-measured clusters located in predefined patterns before being immobilised and enveloped between the carrier and cover material. Whilst the prior art attempts describe approaches to manufacture sandwich structures and mechanism to obtain discrete particulate material pockets, it is believed that the above methods suffer from multiple drawbacks. The prior art methods lack accuracy and repeatability of the absorbent particulate material patterns and have unbalanced pre-metering, metering, forming and transport means. The large and expensive pre-metering, forming and suction means required for the particulate material transport and clustering require very specific customization for each product concept/size/absorbency and are very expensive to design, build, install and replace. These apparatus are furthermore consuming a relative high amount of energy and take significant resources to operate during normal production. The web materials require operating within very narrow tolerances in relation to particle material clustering and depositing and can only operate under relatively limited production speeds, demanding large and complex machinery and installations which are subject to excessive tear, wear, maintenance, cleaning, adjustment, etc. Also, the prior art methods require the carrier layer to be at least sufficiently gas permeable, whilst it would be desired for many applications in fluid handling and storing products such as e.g. baby diapers that the carrier layer would be composed of a liquid and substantially gas impervious barrier layer. Such inefficient and ineffective methods and the complex manufacturing processes makes neither of the prior art methods economically, technically and/or environmentally advantageous.

Hence, there is still a need in the art for a reliable, cost-efficient and maintenance-friendly method and apparatus to consistently dispose, position and pocket particulate materials continuously in a specific, well-defined and discretely arranged pocketing pattern on the surface of a carrier layer moving at a high production speed with limited consumption and/or waste of resources such as e.g. energy and raw materials enduring the production process.

As a result of exhaustive research to address the above-identified and related problems, the inventor have found a more favorable and advantageous manufacturing process to obtain such concepts and structures, which will be explained in greater detail down below.

SUMMARY OF THE INVENTION

As a result of exhaustive research to address the above-identified, derived and related problems, the inventor has found an optimal method and apparatus for the manufacturing of substantially cellulose free absorbent structures immobilising absorbent particulate material allowing fluid management and liquid management in dry, partially and fully liquid loaded state.

The present invention relates in essence to a method for manufacturing a composite structure having a particulate material deposited in a depositing or printing pattern onto a carrier layer and preferably positioned in a pocketing pattern before being immobilised via an auxiliary layer. The method comprises the steps of providing clustering means essentially corresponding with the desired depositing pattern on the moving carrier layer, driving the clustering means in the same direction as and in close proximity to the moving carrier layer, feeding a particle material stream from a particulate material supply means and directing the particle material stream onto the carrier layer. Preferably an additional positioning step is provided by way of a positioning means to stabilise, position and/or reposition the absorbent material in their pocketing pattern before immobilising it in the composite structure. The depositing pattern provided by the clustering means can but does not necessarily have to correspond with the positioning pattern formed by the positioning means. For instance in case of relative homogenous depositing patterns it will preferably not correspond with a discretely clustered positioning pattern. Alternatively the relative dimensions and pattern of the depositing means may for instance be substantially in line with the relative dimensions and pattern of the positioning means, whereby the openings of the depositing means are for instance larger than openings of the positioning means to allow faster printing of the required materials while subsequently optimizing the somewhat blurred printing pattern to avoid the presence of any particulate materials in the attachment regions. Alternatively the openings of the depositing means may be smaller than for instance the openings of the positioning means to allow more accurate printing without depositing any particulate material within the inter-deposit regions allowing easier pocketing. Particulate material such as absorbent particulate polymer material is very suitable to be used in substantially cellulose free absorbent structure for use in an absorbent article such as a disposable hygienic baby diaper or baby made according to the present invention.

In a preferred embodiment a method for producing a composite structure is provided comprising a pattern of particulate material, said method comprising the steps of:
    a—providing at least one essentially endless layer as carrier layer and/or auxiliary layer
    b—providing an essentially endless support means for said carrier layer,
    c—positioning said carrier layer over said support means, whereby said carrier layer is in contact with the contact surface of said support means, and whereby the relative speed between said carrier layer, contact surface of said carrier support means and the clustering means is essentially zero;

d—providing a particulate material stream from a particle material supply means;
e—directing the particulate material through the perforation of a clustering means;
g—combining said carrier layer and said auxiliary layer with said particulate material sandwiched there between;
characterized in that,
h—said clustering means guide said particulate material towards the carrier layer thereby creating a printing pattern of particulate material;
I—said printing pattern being positioned by positioning means thereby forming a pocket pattern of particulate material on the carrier material;
j—and in that the positioning means substantially evacuate particulate material from the inter-pocket pattern zones into the pocket pattern before joining the carrier layer and auxiliary layer to form a pattern of particulate material.

In a preferred embodiment according to the present invention an apparatus is provided for producing a composite structure comprising a pattern of particulate material, said apparatus comprising:
a—a clustering means having a desired perforation pattern
b—a particulate material supplying means positioned to provide particulate materials into the inlet regions of the perforation of said clustering means;
c—a carrier layer supplying means for providing a carrier layer; support means for moving said carrier layer in close proximity to the outlet regions of the clustering means;
d—a positioning means having a desired pocketing pattern
e—transport means for moving said carrier layer with particulate material pattern towards attachment means.

In a preferred embodiment of the invention the clustering means with desired perforation pattern is incorporated into an essentially endless rotating drum, the clustering means can be mounted replaceably onto the rotating drum or can be unitary therewith. The carrier layer is positioned over a substantially endless support means at a carrier speed relative to a fixed frame, whereby the carrier layer is in contact with the support means and whereby the relative speed between carrier layer, the support means and the clustering means and/or drum is preferably essentially zero. The endless support means can have positioning means mounted thereon or can be unitary therewith. A particulate material is provided by a particulate material supply means and the particulate material stream is essentially directed towards the clustering means. The directed particulate material is collected by the inlet regions of the perforations of the clustering means and at least partially held in the outlet region (and/or inlet regions) of the perforations of the clustering means until evacuated. The carrier layer is preferably supported over at least part of the major support means surface area while the particulate material caught and held in the perforations is deposited onto the carrier material.

According to an alternative embodiment of the invention a particulate material is provided via a stationary clustering means located in close proximity of the moving carrier layer. In this alternative embodiment the carrier layer is positioned over a substantially endless support means at a carrier speed relative to the fixed frame, whereby the relative speed between carrier layer and the clustering means is substantially different from zero. In one embodiment the particulate material stream is homogenously directed towards the positioning means, while in another embodiment the particulate material stream is heterogeneously directed via clustering. The homogenous or heterogeneous particulate material will during or after deposit by the depositing means preferably be stabilized, positioned and/or repositioned by positioning means. The carrier layer is preferably supported over at least part of the major support means surface area while the particulate material is directed towards the carrier material.

In an embodiment according to the invention, the resulting composite structure of a carrier layer with discretely deposited (and preferably positioned) particulate material clusters thereon, is complemented with an auxiliary layer, such as for instance non-woven, tissue, paper, thermoplastic material and the like and/or affixed by attachment means, such as for instance glue, bonds, joints and the like, with the particulate material clusters pocketed there between so as to obtain an immobilized sandwich structure usable in the form of an absorbent structure.

In a preferred embodiment the absorbent structure immobilizes, retains and/or restrains the particulate material and the attachments seal, bond and/or join at least part of the outer layers of the composite structure together via ultrasonic bonding, thermo-bonding, pressure-bonding and/or glue-bonding means. These attachments preferably form and/or define pockets which contain particulate material, whereby the attachment regions comprise essentially and preferably no particulate material. Preferably the absence of an excess or the complete elimination of synthetic immobilisation admixtures (e.g. adhesive and binders, such as thermoplastic glues and webs) used for covering, restraining or bonding absorbent polymers makes the structure technically, environmentally and economically very favourable. In an alternative embodiment however, the composite structure is covered with such thermoplastic materials, glues, binders and/or adhesives to fixate, pocket, encapsulate, bind and/or join these particulate material clusters to and/or in between one or more layers. Additional materials and/or layers to provide extra functional and/or structural advantages such as strength, acquisition, absorption, distribution, transport, retention, etc. may also be incorporated.

In a preferred embodiment according to the invention, a process for providing a structure comprising of a carrier layer, a particulate material and an auxiliary layer is provided, whereby the particulate material is at least partially enclosed by a carrier and auxiliary layer so as to form an composite structure, comprising the steps of prior to joining the carrier layer to the auxiliary layer positioning the deposited particulate material through a positioning means, preferably being airflows. In one embodiment, the particulate material is deposited substantially homogeneously on the carrier layer prior to subsequently positioning it via the positioning means to discretely and heterogeneously positioned particulate material clusters. In a preferred embodiment, the particulate material comprises absorbent polymer material for body exudates and/or skin care material such as ion exchange resins, deodorant, anti-microbial agents, binder particles or other beneficial particles.

An absorbent structure manufactured according to this preferred embodiment of the invention has attachments characterized by improved attachment properties. This is advantageous as it provides increased efficiency and effectiveness of the used attachment means, thereby increasing attachment quality, quantity and/or utilisation of attachment energy or materials which is crucial in the high speed and low cost manufacturing of absorbent articles containing such absorbent structures in light specified absorption, distribution, retention performance while minimizing rewet, leakages and structural failures.

During the depositing process, the particulate material is directed to the carrier layer. If the particulate material is spread homogeneously, the probability that a small piece of particulate material is positioned in an area which is intended to serve as an attachment area between the carrier layer and the auxiliary layer, is given by $P_{normal}=B/(A+B)$, where "B" is the attachment area on a piece of the carrier layer and "A" is the area on the same piece of the carrier layer which is not to be attached to the auxiliary material. According to a preferred method according to the present invention particulate material is non-homogeneously deposited prior to attaching the carrier layer to the auxiliary layer, such that the probability $P_{inv}$ of a smaller piece of particulate material is deposited in an attachment area is smaller than $P_{normal}$: $P_{inv}<P_{normal}$, preferably $P_{inv}<0.5*P_{normal}$, more preferably $P_{inv}<0.1*P_{normal}$, even more preferably $P_{inv}<0.05*P_{normal}$, still even more preferably $P_{inv}<0.01*P_{normal}$, most preferably $P_{inv}<0.001*P_{normal}$. Decreasing the possibility $P_{inv}$ is advantageous for the attachment process, since the presence of particulate material in or on the attachment area may lead to a less strong attachment between carrier layer and auxiliary layer. Obviously the more accurate the depositing requirements of the particulate materials will have to be the slower and/or more difficult the positioning step will be during industrial manufacturing of composite structures according to the present invention. Hence the favourable positioning means allow for a less accurate depositing as via this positioning step the incorrectly or inaccurately deposited particulate materials are repositioned towards their intended position by way positioning and repositioning of the particulate materials. Additional correctly and accurately deposited particulate materials are stabilized to be kept in their intended position by way of these same positioning means allowing correct pocketing and immobilisation of all particulate materials without inferior attachment properties imparted by migrated, misplaced or lost particulate materials.

According to another aspect of the present invention an apparatus for producing a composite structure comprising particulate material clusters there between is provided. Said apparatus comprises a clustering means having a desired depositing pattern, a particulate material supplying means positioned to provide particulate materials into the inlet regions of the perforations of said clustering means, a carrier layer supplying means for providing a carrier layer, support means for moving said carrier layer in close proximity to the outlet regions of the clustering means and transport means for moving said carrier layer with particulate material clusters away from the clustering means. Preferably further positioning means are foreseen to position the absorbent material in their optimal pocket position before immobilising them in the composite structure. The positioning means can be mounted on or can be unitary with the support means and/or transport means.

The clustering means are preferably arranged to catch, collect, hold and deposit the particulate materials from the particulate material stream as provided by the particulate supply means. The perforations within the clustering means are designed so as to catch and collect the particulate material stream by way of the inlet regions, and preferably converge the particulate materials towards the outlet regions so as to accumulate and build up particulate material clusters within the perforations ready for deposit onto the carrier layer, preferably in discrete printing patterns of particulate material clusters. It will be apparent that the perforations of the clustering means can be made up from all available alternatives known from the art such as hollow rectangles, cones, tubes and any other suitable format to direct the particulate material to the carrier layer.

The support means brings the carrier layer into a depositing position of, preferably in close proximity to, most preferably in contact with, the outlet regions of the perforations of the clustering means. Preferably a selected level of pressure contact in between the deposit surface of the carrier layer and the outer contact surface of the clustering means is provided, so as to lock the discrete particulate material clusters until deposited onto the deposit surface of the carrier layer. In an alternative embodiment, no substantial pressure contact in between the deposit surface of the carrier layer and the outer contact surface of the clustering means is provided, and the particulate material provided via the particulate material stream is immediately caught, collected and deposited upon the carrier layer. Preferably additional positioning means are foreseen to stabilise, position and/or reposition the deposited particulate material clusters in their final pocketing position and pattern before being immobilized. A transport means moves the carrier layer and the particulate materials away.

In a preferred embodiment the particulate material clusters deposited, and preferably positioned, onto the carrier layer are covered by an auxiliary layer via a covering means so as to form for instance an absorbent polymer material area. In a more preferred embodiment, the particulate material clusters from the composite structure are relatively immobilised, bound, joined and/or otherwise restrained in between a carrier layer and any suitable auxiliary layer. Preferably, attachment means leading to a composite sandwich structure of a carrier layer and auxiliary layer with particulate material clusters enclosed and/or immobilised, bound, join and/or restrained there between in the form of pockets or compartment are provided.

Preferably the particulate material supply means comprises a vibrating, coiling and/or turning means so as to accurately, continuously and controllably provide the required particulate material amounts, sizes and/or speeds towards the clustering means. It is furthermore preferred, that the particulate material is being transported in between such vibrating, coiling and/or turning means and the clustering means by way of a feeding tube means, which can alternatively be arranged with gas pressure means to guide and direct the particulate material stream to the inlet regions of the clustering means. In a preferred embodiment, the feeding tube is substantially longitudinal, vertically and/or converging and the particulate material has substantial weight so that one can use gravity to transport the particles through the feeding tube into the clustering means. However, additional conveyer means such as mechanical (such as airflows), electro-magnetic (such as magnets in case the particles interact with a magnetic field), electro-static (such as particulate material and/or conveyer charging) and/or other means can be used to help convey particulate material stream towards the clustering means.

In a preferred embodiment, a dosing means of a volumetric, gravimetric or other type is used so as to control the quantity, size and/or speed of particles entering the feeding tube means is provided. It is further preferred that the particulate material stream can be redirected via control means into removing means so as to be moved again towards the particulate supply means via recovery tubing means for re-use and/or less preferably guided out of the production system via collection means to be moved towards separate storage facilities for later usage and/or disposal in case irreparably damaged, contaminated, spoiled and/or rendered unusable.

In a preferred embodiment, the clustering means are unitary with a substantially endless rotating drum, preferably having a cylinder-like outer shell. In a preferred embodiment an endless rotating drum with replaceable, customisable and/or adjustable clustering means is provided. Alternatively the clustering means are stationary clustering means. The clustering means are in line with the opening of the feeding tube means thereby directing the particulate materials to fall, be guided, directed, pushed and/or vacuumed through the respective inlet regions and/or outlet regions of the perforation pattern of the clustering means to obtain the desired depositing or printing pattern. It is understood that the clustering means can have any sort and number of perforations and patterns, whereby the amount of perforations goes from at least one perforation to any suitable numbers of perforations in light of the envisaged composite structure. In case one perforation its dimension may be similar to feeding tube.

It is preferred to under-fill (or, eventually 'right-fill') the perforations of the clustering means. Using a particle material supply means with a preferably gravimetric dosing system in combination with a feeding tube means such as a tube, pipe or conveyer of the right dimensions and shape will then ensure that the proper weights are supplied, gathered in the perforations and deposited by the outlet regions so as to form the desired printing pattern of particulate material clusters as stipulated by the perforation pattern of the clustering means.

In a preferred embodiment, the inlet regions are of a funnel-like shape with steep slopes separated from one another by sharp ridges so no substantial amounts of particulate materials remain caught in between the inlet regions and/or on the slopes of the inlet regions, but are readily transported towards the outlet regions for scheduled deposit on the carrier material. In a preferred embodiment, a combination of larger and smaller inlet regions and outer regions are provided leading to more homogenous, heterogeneous or complex perforation patterns.

Preferably the void volume of the perforations is larger than the volumes of particulate material one wants to print, to prevent overfilling of the clustering means during the production process. In this case of correctly designed clustering means and a fully, effectively and efficiently working apparatus one can also greatly increase accuracy and reliability of the manufacturing process and thereby also eliminating the need for a sweeping means, thus optimising raw material usage, limiting investment cost and reducing maintenance cost. However in case required, any 'overfill', migration and/or misplacement of particulate material can be guided and/or redirected via sweeping means, such as scrapers, brushes, air blow, vacuum suction, etc, into one or more available inlet regions of the cluster means and/or be guided into recovery means or collection means so as to be moved away from the clustering means for re-use, collection and/or disposal. This redirecting greatly increases process efficiency.

As also described in EP priority application 10447020.8 and hereby incorporated by reference, an absorbent sandwich-like structure is provided which comprises a distribution layer with an absorbent capacity and an immobilisation layer which joins to the distribution layer to define compartments there between containing intermediate absorbent material. In particular an absorbent structure for use in an absorbent article comprises a distribution layer having an absorbent capacity of at least about 5 g/m$^2$, an immobilisation layer which is joined to the distribution layer to define compartments there between, and an absorbent material held in at least one of the compartments, wherein said absorbent material comprises an absorbent polymer material and from zero to an amount less than about 40 weight percent absorbent fibrous material, based on the weight of absorbent polymer material. The absorbent structure provides in particular an increased fluid communication structure including better adsorption and dispersion in and between the absorbent polymer material pockets, due to the additional wicking and mass flow of liquids caused by the distribution layer, limiting gel blocking, reducing rewet and minimizing leakages. It further provides for a method and apparatus to produce such absorbent structures at high production speed with low energy and raw material consumption.

As also described in EP priority application 10447021.6 and hereby incorporated by reference, an absorbent sandwich-like structure is provided which comprises a substantially liquid-impermeable wicking layer and an immobilisation layer which joins to the wicking layer to define compartments there between containing intermediate absorbent material. In particular an absorbent structure for use in an absorbent article comprises a substantially liquid-impermeable wicking layer, and an immobilisation layer which is joined to the substantially liquid-impermeable wicking layer to define compartments there between, and an absorbent material held in at least one of the compartments, wherein said absorbent material comprises an absorbent polymer material, and from zero to an amount less than about 40 weight percent absorbent fibrous material, based on the weight of absorbent polymer material. The substantially liquid-impermeable wicking layer allows unbound liquids such as water, urine and/or other bodily exudates to more easily spread out, which allows better distribution and transport so as to wet the side and lower sides of the absorbent polymer materials within the pockets. It ensure lower rewet values, less leakage risk and less surface wetness and thus increased reliability of the overall structure. It further provides for a method and apparatus to produce such absorbent structures at high production speed with low energy and raw material consumption.

As also described in EP priority application 10447022.4 and hereby incorporated by reference, an absorbent sandwich-like structure is provided which comprises a carrier layer, an auxiliary layer and an intermediate absorbent particulate material there between wherein substantially primary attachments and substantially secondary attachments join the carrier layer and auxiliary layer together, whereby the secondary attachments are loosened as a result of exposing the absorbent structure to liquid whereas the primary attachments remain substantially intact. It further provides for a method and apparatus to produce such absorbent structures at high production speed with low energy and raw material consumption.

As also described in EP priority application 10447023.2 and hereby incorporated by reference, an absorbent sandwich-like structure is provided which comprises a carrier layer, an auxiliary layer and an intermediate absorbent material there between wherein substantially permanent primary attachments and substantially temporary secondary attachments join the carrier layer and auxiliary layer together, whereby the absorbent structure is made to in-homogeneously swell as a result of exposing the absorbent structure to liquid to form a liquid-managing surface structure. It further provides for a method and apparatus to produce such absorbent structures at high production speed with low energy and raw material consumption.

As also described in EP priority application 10447024.0 and hereby incorporated by reference, a method and apparatus is provided for forming a sandwich-like structure, by depositing particulate material in a desired pattern onto a moving carrier layer. In particular a method for depositing particulate material in a desired pattern onto a moving carrier layer is provided, which provides a clustering means with perforations corresponding to a desired pattern, driving the clustering means in the same direction as and in close proximity to the moving carrier layer, feeding a particle material stream from a particulate material supply means and directing the particle material stream through the clustering means onto the carrier layer. Preferably the particulate materials are clustered via the inlet regions of the perforations and released via the outlet regions of the clustering means. The method allows accurate forming of a predetermined pattern of particulate material clusters at high production speed, with reduced raw material usage and relative low cost. It furthermore provides the improved thin, flexible, lightweight particulate material absorbent structures with discretely deposited particulate material clusters thereon, complemented with an auxiliary layer, such as for instance non-woven, tissue, paper, thermoplastic material and the like and/or affixed by attachment means, such as for instance glue, bonds, joints and the like, with particulate material clusters relatively immobilized there between so as to obtain a sandwich structure usable in the form of an absorbent structure.

As also described in EP priority application 10447027 and hereby incorporated by reference, a method and apparatus is provided for forming a sandwich-like structure, by positioning particulate material in a desired pattern onto a moving carrier layer. In particular a method for positioning particulate material in a desired pattern onto a moving carrier layer is provided, providing a first material, an intermediate material and a second material, whereby prior to joining the first material to the second material, the distribution of the intermediate particulate material is altered through an airflow. In a preferred embodiment the intermediate particulate material is provided substantially homogeneously on the first material prior to applying the positioning airflow. When the intermediate material is undesirable in the attachment area, the method describes the use of airflows, resulting from blowing and/or suction holes to evacuate the intermediate material from the attachment area prior to or during bonding, leading to improved and controllable attachment properties, thus increasing attachment quality and utilisation of energy or materials. It furthermore provides improved thin, flexible, lightweight absorbent particulate structures.

The method and apparatus according to preferred embodiments of the invention leads to highly appreciated thin, flexible and/or light-weight absorbent structures which are economically, environmentally, technically and/or commercially advantageous, not in the least since they are obtained without the need for substantial and bulky amounts of fibrous absorbent materials such as fluff and wood pulp (allowing "fluffless" advertisement claims) and are not using substantial and expensive amounts of glue, binder, adhesive and/or other thermoplastic materials (allowing "glueless" advertisement claims). This is unprecedented within the prior art.

DETAILED DESCRIPTION OF THE INVENTION

Figure 1A:
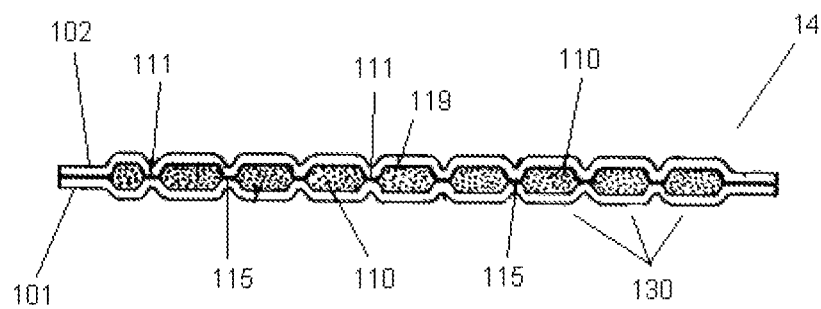
FIG. 1A-D provides cross-sectional schematic illustrations of absorbent structures made according to embodiments of the invention.

The present invention relates to a method and apparatus for creating composite structures comprising particulate material, preferably absorbent particulate material such as absorbent polymer materials, more preferably absorbent particulate polymer material; preferably clustered, enveloped and/or immobilised in between a carrier layer and auxiliary layer, possibly via primary and secondary attachment means, so as to form discrete and predetermined pocketing patterns of particulate material sheets for use in absorbent products, preferably a disposable absorbent article from the personal hygiene industry, such as feminine hygiene garments, baby diapers and pants and adult incontinence garments.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, insofar such variations are appropriate to perform in the disclosed invention. However, it is to be understood that the value to which the modifier "about" refers is itself also specifically disclosed.

"Absorbent article", "absorbent garment", "absorbing article", "absorbing garment", and the like as used herein are used interchangeably and refer to devices that absorb and contain bodily exudates, and more specifically, refers to devices that are placed against or in proximity to the body of the wearer to absorb and contain the various liquids discharged from the body. Absorbent articles include but are not limited to feminine hygiene garments, baby diapers and pants, adult incontinence garments, various diaper and pants holders, liners, towels, absorbent inserts and the like.

"Absorbent component" as used herein refers to a structural constituent of an absorbent structure, e.g., a piece of an absorbent core, such as one of multiple pieces in a multi-piece absorbent core.

"Absorbent element" as used herein refers to a part of a functional constituent of an absorbent structure, e.g., a liquid acquisition layer, a liquid distribution layer, or a liquid storage layer formed of a material or materials having particular liquid handling characteristics suitable for the specific function.

"Absorbent insert" as used herein refers to a device adapted for insertion into an absorbent article and to serve as an absorbent structure when so inserted.

"Absorbent layer" as used herein refers to a term referring to a discrete, identifiable sheet-like or web-like element of an absorbent structure which may remain detached and relatively movable with respect to another such element or may be attached or joined so as to remain permanently associated with another such element. Each absorbent layer may itself include a laminate or combination of several layers, sheets and/or webs of similar or diverse compositions.

"Absorbent polymer material", "absorbent gelling material", "AGM", "superabsorbent", "superabsorbent material", "super absorbent polymer", "SAP" and the like as used herein are used interchangeably and refer to any suitable particulate (e.g., flaked, particulate, granular, or powdered) or fibrous cross linked polymeric materials that can absorb at least 5 times and preferably at least about 10 times or more its weight of an aqueous 0.9% saline solution as measured using the Centrifuge Retention Capacity test (EDANA 441.2-01).

"Absorbent polymer material area" as used herein refers to the area of the absorbent structure wherein adjacent layers are separated by a multiplicity of absorbent polymer material. Incidental contact areas between these adjacent layers within the absorbent particulate polymer material area may be intentional (e.g. bond area's) or unintentional (e.g. manufacturing artifacts).

"Absorbent particulate polymer material" as used herein refers to an absorbent polymer material which is in particulate form such as powders, granules, flakes and the like so as to be flowable in the dry state.

"Absorbent structure" as used herein refers to those elements of an absorbent article comprising material or a combination of materials suitable to absorb, distribute and retain bodily exudates.

"Absorption" as used herein refers to the process by which a liquid is taken up within a material.

"Acquisition layer", "acquisition region", "acquisition surface" or "acquisition material" and the like as used herein refer to a layer having a faster liquid uptake capability.

"Absorbency" is the ability of a material to take up fluids by various means including capillary, osmotic, solvent, chemical or other action.

"Adult incontinence garment" as used herein refers to absorbent articles intended to be worn by incontinent adults, for absorbing and containing bodily exudates.

"Adhesion" as used herein refers to the force that holds different materials together at their interface.

"Adhesive" as used herein refers to a material, which may or may not be flowable in solution or when heated, that is used to bond materials together.

"Adsorption" as used herein refers to the process by which a liquid is taken up by the surface of a material.

"Airlaying" as used herein refers to forming a web by dispersing fibres or particles in an air stream and condensing them from the air stream onto a moving screen by means of a pressure or vacuum; a web of fibres produced by air laying is herein referred to an "airlaid"; an airlaid web bonded by one or more techniques to provide fabric integrity is herein referred to an "airlaid non-woven".

"Apparent density", "density" and like as used herein refers to the basis weight of the sample divided by the caliper with appropriate unit conversions incorporated therein. Apparent density used herein has the unit g/cm$^3$.

"Attach", "attached" and "attachment" as used herein are synonymous with their counterparts of the terms "fasten", "affix", "secure", "bind", "join" and "link".

"Baby diaper" as used herein refers to absorbent articles intended to be worn by children, for absorbing and containing bodily exudates which the user draws up between the legs and fastens about the waist of the wearer.

"Baby pants" as used herein refers to absorbent articles marketed for use in transitioning children from diapers to underwear intended to cover the lower torso of children, so as to absorb and contain body exudates which article is generally configured like a panty garment and manufactured with a completed waist encircling portion, thereby eliminating the need for the user to fasten the article about the waist of the wearer.

"Back region" as used herein refers to the portion of an absorbent article or part thereof that is intended to be positioned proximate the back of a wearer.

"Backing" as used herein refers to a web or other material that supports and reinforces the back of a product.

"Basis weight" is the weight per unit area of a sample reported in grams per square meter, $g/m^2$ or gsm.

"Bodily exudates", "body exudates", "bodily fluids", "body fluids", "bodily discharges", "body discharges", "liquids" and the like as used herein are used interchangeably and refer to, but are not limited to urine, blood, vaginal discharges, breast milk, sweats and fecal matter.

"Binder", "adhesive", "glue", "resins", "plastics" and the like as used herein are used interchangeably and refer to substances, generally in a solid form (e.g. powder, film, fibre) or as a foam, or in a liquid form (e.g. emulsion, dispersion, solution) used for example by way of impregnation, spraying, printing, foam application and the like used for attaching or bonding functional and/or structural components, elements and materials, for example including heat and/or pressure sensitive adhesives, hot-melts, heat activated adhesives, thermoplastic materials, chemical activated adhesives/solvents, curable materials and the like.

"Bond strength" as used herein refers to the amount of adhesion between bonded surfaces. It is a measure of the stress required to separate a layer of material from the base to which it is bonded.

"Capillary action", "capillarity", or "capillary motion" and the like as used herein are used to refer to the phenomena of the flow of liquid through porous media.

"Chassis" as used herein refers to a foundational constituent of an absorbent article upon which the remainder of the structure of the article is built up or overlaid, e.g., in a diaper, the structural elements that give the diaper the form of briefs or pants when configured for wearing, such as a backsheet, a topsheet, or a combination of a topsheet and a backsheet.

"Cellulose fibres" as used herein refers to naturally occurring fibres based on cellulose, such as, for example cotton, linen, etc; wood pulp fibres are one example of cellulose fibres; man-made fibres derived from cellulose, such as regenerated cellulose (rayon), or partially or fully acetylated cellulose derivatives (e.g. cellulose acetate or triacetate) are also considered as cellulose fibres.

"Cluster" or the like as used herein refers to an agglomeration of particles and/or fibres.

"Chemically stiffened fibres", "chemically modified fibres", "chemically cross-linked fibres", "curly fibres" and the like as used herein are used interchangeably and refer to any fibres which have been stiffened by chemical means to increase stiffness of the fibres under both dry and aqueous conditions, for example by way of addition of chemical stiffening agents (e.g. by coating, impregnating, etc), altering the chemical structure of the fibres themselves (e.g. by cross-linking polymer chains, etc) and the like.

"Cohesion" as used herein refers to the resistance of similar materials to be separated from each other.

"Compartment" as used herein refers to chambers, cavities, pockets and the like.

"Comprise," "comprising," and "comprises" and "comprised of" as used herein are synonymous with "include", "including", "includes" or "contain", "containing", "contains" and are inclusive or open-ended terms that specify the presence of what follows e.g. a component and do not exclude or preclude the presence of additional, non-recited components, features, elements, members, steps, known in the art or disclosed therein.

"Coverstock" as used herein refers to a lightweight non-woven material used to contain and conceal an underlying absorbent core material; examples are the facing layer or materials that cover the absorbent cores of feminine hygiene garments, baby diapers and pants and adult incontinence garments.

"Crotch region" of an absorbent article as used herein refers to about 50% of the absorbent article's total length (i.e., in the y-dimension), where the crotch point is located in the longitudinal centre of the crotch region. That is, the crotch region is determined by first locating the crotch point of the absorbent article, and then measuring forward and backward a distance of 25% of the absorbent article's total length.

"Cross direction (CD)", "lateral" or "transverse" and the like as used herein are used interchangeably and refer to a direction which is orthogonal to the longitudinal direction and includes directions within ±45° of the transversal direction.

"Curing" as used herein refers to a process by which resins, binders or plastics are set into or onto fabrics, usually by heating, to cause them to stay in place; the setting may occur by removing solvent or by cross-linking so as to make them insoluble.

"Diaper", "conventional diaper", "diaper-like", "diaper-like garment" and the like as used herein are used interchangeably and refer to disposable absorbent articles, which typically include a front waist portion and a back waist portion which may be releasably connected about the hips of the wearer during use by conventional fasteners such as adhesive tape fasteners or hook and loop type fasteners. In use, the article is positioned between the legs of the wearer and the fasteners are releasably attached to secure the back waist portion to the front waist portion of the diaper, thereby securing the diaper about the waist of the wearer. The front waist portion and a back waist portion are connected by relatively non-stretchable or stretchable members (the term "stretchable" as used herein refers to materials that are extensible when forces are applied to the material, and offer some resistance to extension). Hence, such articles are generally not configured to be pulled up or down over the hips of the wearer when the fasteners are attached.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Distribution layer", "distribution region", "distribution surface" or "distribution material" and the like as used herein are used interchangeably and refer to a layer having a larger capacity in wicking, dispersing and distributing liquids.

"Dry laying" as used herein refers to a process for making a non-woven web from dry fibre; these terms apply to the formation of carded webs, as well as to the air laying formation of random webs; a web of fibres produced by dry laying is herein referred to as a "drylaid"; a drylaid web bonded by one or more techniques to provide fabric integrity is herein referred to a "drylaid non-woven".

"Dry strength" as used herein refers to the strength of an adhesive joint determined in dry state conditions, immediately after drying under specified conditions or after a period of conditioning in the standard laboratory atmosphere.

"Fabric" as used herein refers to a sheet structure made from fibres, filaments and/or yarns.

"Feminine hygiene garments" as used herein refer to absorbent hygiene articles intended to be worn by woman, for absorbing and containing body exudates.

"Fibre" as used herein refers to the basic threadlike structure from which non-woven, yarns and textiles are made. It differs from a particle by having a length at least 4 times its width; "Natural fibres" are either of animal (wool, silk), vegetable (cotton, flax, jute) or mineral (asbestos) origin, while "Man-made fibres" may be either polymers synthesised from chemical compounds (polyester, polypropylene, nylon, acrylic etc.) or modified natural polymers (rayon, acetate) or mineral (glass). "Fibre" and "filament" are used interchangeably.

"Film", "foil" and the like as used herein are used interchangeably and refer to a thin sheet of essentially non-absorbent material such as plastic or closed foams. In this invention it particularly refers to materials that do not correspond to non-woven.

"Fluff pulp" as used herein refers to wood pulp specially prepared to be dry laid.

"Front region" as used herein refers to the portion of an absorbent article or part thereof that is intended to be positioned proximate the front of a wearer.

"Garment facing layer" as used herein refers to elements of the chassis that form the outer surface of the absorbent article, such as the back sheet, the side panels, the waist fasteners, and the like, when such elements are present.

"Heat activated adhesive" as used herein refers to a dry adhesive that is rendered tacky or fluid by application of heat or heat and pressure to the assembly.

"Heat sealing adhesive" as used herein refers to a thermoplastic adhesive which is melted between the adherent surfaces by heat application to one or both of the adjacent adherent surfaces.

"Highloft" as used herein refers to general term of low density, thick or bulky fabrics.

"Hot-melt adhesive" as used herein refers to a solid material that melts quickly upon heating, then sets to a firm bond upon cooling; used for almost instantaneous bonding.

"Hydrophilic" as used herein refers to having an affinity for being wetted by water or for absorbing water.

"Hydrophobic" as used herein refers to lacking the affinity for being wetted by water or for absorbing water.

"Immobilisation layer" as used herein refers to a layer able to be applied to the particulate material with the intent to immobilize, bond, join and/or restrain particulate material.

"Join", "joined" and "joining" as used herein refers to encompassing configurations wherein an element is directly secured to another element by affixing the element directly to the other element, as well as configurations wherein the element is indirectly secured to the other element by affixing the element to an intermediate member or members which in turn is or are affixed to the other element.

"Knitting" as used herein refers to the technique for interlocking loops of fibres with needles or similar devices.

"Layer" refers to identifiable components of the absorbent article, and any part referred to as a "layer" may actually comprise a laminate or combination of several sheets or webs of the requisite type of materials. As used herein, the term "layer" includes the terms "layers" and "layered." "Upper" refers to the layer of the absorbent article which is nearest to and faces the wearer facing layer; conversely, the term "lower" refers to the layer of the absorbent article which is nearest to and faces the garment facing layer. "Layer" is three dimensional structure with a x dimension width, y dimension length, and z-dimensions thickness or caliper, said x-y dimensions being substantially in the plane of the article, however it should be noted that the various members, layers, and structures of absorbent articles according to the present invention may or may not be generally planar in nature, and may be shaped or profiled in any desired configuration.

"Machine direction (MD)", "longitudinal" and the like as used herein are used interchangeably and refer to a direction running parallel to the maximum linear dimension of the structure and includes directions within ±45° of the longitudinal direction.

"Major surface" as used herein refers to a term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

"Mass flow" as used herein refers to the flow of a liquid from one absorbent element or component to another absorbent element or component by channel flow action.

"Mechanical bonding" as used herein refers to a method of bonding fibres by entangling them. This can be achieved by needling, stitching with fibres or by the use of high-pressure air or water jets and the like.

"Non-woven" as used herein refers to manufactured sheet, web or batt of directionally or randomly orientated fibres, bonded by friction, and/or cohesion and/or adhesion, excluding paper and products which are woven, knitted, tufted, stitch-bonded incorporating binding yarns or filaments, or felted by wet-milling, whether or not additionally needled. The fibres may be of natural or man-made origin and may be staple or continuous filaments or be formed in situ.

Commercially available fibres have diameters ranging from less than about 0.001 mm to more than about 0.2 mm and they come in several different forms: short fibres (known as staple, or chopped), continuous single fibres (filaments or monofilaments), untwisted bundles of continuous filaments (tow), and twisted bundles of continuous filaments (yarn). Non-woven fabrics can be formed by many processes such as melt blowing, spun bonding, solvent spinning, electro spinning, and carding. The basis weight of non-woven fabrics is usually expressed in grams per square meter (gsm).

"Pant", "training pant", "closed diapers", "prefastened diapers", "pull-on diapers" and "diaper-pants" and the like as used herein are used interchangeably and refer to absorbent articles which are typically applied to the wearer by first leading the feet into the respective leg openings and subsequently pulling the pants from the feet to waist area over the hips and buttocks of the wearer and which are capable of being pulled up or down over the hips of the wearer. Typically, such articles may include a front waist portion and a back waist portion which may be connected about the hips of the wearer by integral or releasable members. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened).

"Polymer" as used herein refers to but is not limited to, homopolymers, copolymers, such as for example, block, graft, random and alternating copolymers, terpolymers, etc. and blends and modifications thereof. Unless otherwise specifically limited, the term "polymer" includes all possible spatial configurations of the molecule and include, but are not limited to isotactic, syndiotactic and random symmetries.

"Rear" as used herein refers to the portion of an absorbent article or part thereof that is intended to be positioned proximate the back of the wearer.

"Resin" as used herein refers to a solid or semisolid polymeric material.

"Substantially cellulose free" as used herein refers to an absorbent article, structure or core, that contains less than 40% by weight cellulosic fibres, less than 20% cellulosic fibres, less than 5% cellulosic fibres, no cellulosic fibres, or no more than an immaterial amount of cellulosic fibres which do not materially affect the thinness, flexibility or absorbency thereof. This definition also encompasses fully cellulose free whereby the percentage is 0%.

"Thermobonding" as used herein refers to a method of bonding fibres by the use of heat and/or high-pressure.

"Thermoplastic" as used herein refers to polymeric materials that have a melting temperature and can flow or be formed into desired shapes on the application of heat at or below the melting point.

"Ultrasonic" as used herein refers to the use of high frequency sound to generate localised heat through vibration thereby causing fibres to bond to one another.

"Water-absorbing", "liquid-absorbing", "absorbent", "absorbing" and the like as used herein are used interchangeably and refer to compounds, materials, products that absorb at least water, but typically also other aqueous fluids and typically other parts of bodily exudates such as at least urine or blood.

"Wearer facing layer" as used herein refers to elements of the chassis that form the inner surface of the absorbent article, such as the topsheet, the leg cuffs, and the side panels, etc., when such elements are present.

"Weaving" as used herein refers to the process of interlacing two or more sets of yarns at right angles to form a fabric; a web of fibres produced by weaving is herein referred to as a "Woven".

"Web material" as used herein refers to an essentially endless material in one direction, i.e. the longitudinal extension or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Typically, the width of web materials (the y-direction) will be significantly larger than the thickness, but less than the length. Often, though not necessarily, the thickness and the width of such materials is essentially constant along the length of the web. Without intending any limitation, such web materials may be cellulosic fibre materials, tissues, woven or non-woven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, non woven/film laminates. Web materials may comprise other materials, such as added binding material, particles, hydrophilizing agents and the like.

"Wet burst strength" is a measure of a layer's ability to absorb energy, when wet and subjected to deformation normal to the plane of the web.

"Wet strength" as used herein refers to the strength of an adhesive joint determined immediately after removal from a liquid in which it has been immersed under specified conditions of time, temperature and pressure. The term is commonly used in the art to designate strength after immersion in water.

"Wet laying" as used herein refers to the forming a web from an aqueous dispersion of fibres by applying modified paper making techniques; a web of fibres produced by wetlaying is herein referred to as a "wetlaid".

"Wood pulp" as used herein refers to cellulosic fibres used to make viscose rayon, paper and the absorbent cores of products such as feminine hygiene garments, baby diapers and pants and adult incontinence garments.

"X-y dimension" as used herein refers to the plane orthogonal to the thickness of the article, structure or element. The x- and y-dimensions correspond generally to the width and length, respectively, of the article, structure or element.

"Z-dimension" as used herein refers to the dimension orthogonal to the length and width of the article, structure or element. The z-dimension corresponds generally to the thickness of the article, structure or element.

The recitation of numerical ranges by endpoints includes all numbers and fractions subsumed within that range, as well as the recited endpoints. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

It will be apparent to one of ordinary skill in the art that the method and apparatus according to the present invention may be used to obtain composite structures, absorbent structures which may be used in absorbent articles, and more particularly, in disposable absorbent articles, such as feminine hygiene garments, baby diapers and pants and adult incontinence garments. Accordingly, the present invention shall not be limited to the method, apparatus, absorbent structures and absorbent articles specifically described and illustrated herein, although the following description is particularly directed to manufacture of composite structures and absorbent structure for absorbent disposable baby diaper products.

The present invention was based upon the findings that products resulting from a method and apparatus to create a composite structure comprising particulate material deposited in a pre-designed and controlled patterns, can be more efficiently used to absorb, distribute and retain liquid. Absorbent articles, such as feminine hygiene garments, baby diapers and pants and adult incontinence garments absorb, distribute, transport and contain bodily exudates. They also are intended to prevent bodily exudates from leaking, soiling, wetting or otherwise contaminating clothing or other articles, such as bedding, that come in contact with the wearer. A disposable absorbent article, such as a disposable diaper, may be worn for several hours in a dry state or in bodily exudates loaded state. Accordingly, efforts have been made toward improving the fit and comfort of the absorbent article to the wearer, both when the article is dry and when the article is fully or partially loaded with body exudates, while maintaining or enhancing the absorbing and containing functions of the article.

Some absorbent articles, like diapers, contain a particulate material, such as an absorbent polymer material, more preferably an absorbent particulate polymer material. Although such absorbent particulate material absorbs liquid and swells, it is more effective when disposed in an absorbent structure in a certain pattern or arrangement when intending optimal absorbency, fit and/or comfort. Since it is desirable for absorbent particulate material to remain in its intended location in an absorbent article, such particulate materials are to be clustered and are desirably relatively immobilized in the absorbent article such that the absorbent particulate material remains immobilized, bonded, joined and/or restrained on their intended location when the absorbent article is dry, partially wetted and/or fully wetted.

In addition to being absorbent, absorbent articles, such as diapers, are desirably thin, flexible and/or light-weight, for ease and comfort in use and for more convenient and neat packaging and storage. Absorbent articles, which may often be used in large quantities, may also desirably be inexpensive. Some technologies of clustering and immobilizing absorbent particulate polymer material in an absorbent article such as additional fluff, add bulk to the absorbent article and thereby increase thickness, reduce flexibility, and/or increase cost of the absorbent article. Other technologies for immobilizing absorbent particulate polymer material in an absorbent article may not be as effective in maintaining immobilization when the absorbent article is in the wet state as when in the dry state. Accordingly, there remains a need for a method and apparatus which can dose the absorbent particulate material in specified quantities, deposit, position and pocket it in a desired pattern so that thin, flexible, and/or inexpensive absorbent article can be obtained.

There are many technologies for attaching two functional and/or structural layers, components, elements and/or materials together. Some of them incorporate the use of heat and/or pressure sensitive adhesives such as for instance hot-melts, cold-melts, heat activated adhesives, thermoplastic materials, chemical activated adhesives/solvents, curable materials and the like, where the adhesives create the attachments between the respective materials, others involve thermo-mechanical methods such as for instance heat-sealing, pressure-sealing or ultrasonic sealing processes where energy transfer partially links, melts or fuses multiple materials to and into each other. Correctly applying these methods and processes is increasingly more difficult, inefficient and/or ineffective at higher production speed in the presence of particulate materials, for such particulate materials can occasionally or unwillingly get in between the pocketing materials to be attached, distort the attachment process and/or reduce the strength and quality of these attachments and/or the quantity of the functional attachments. This is specifically the case if the intermediate material is of a flowable, fibrous or granular nature. A small particle or fiber or a lightweight flat layer can easily, due to manufacturing process fluctuations, migrate within the article or structure around those elements which are still substantially unattached. If intermediate material—even partially—ends up in the attachment area, it can or may reduce the effectiveness, efficiency and/or strength of said attachment or attachment method. This can be by reducing the attachment surface, by impeding an efficient energy transfer, by creating undesirable chemical reactions or physical effects and the like. A reduced attachment strength or integrity may also be due to a weaker internal strength of the particulate material which would then act as weakest link within the structure and/or due to the abrasive nature of the particulate material allowing easier rupture and/or tearing and/or loss of strength of the attachments between the respective other materials. It may also lead to a higher consumption of the particulate materials and/or other raw materials and thus lead to a loss of efficiency and increase in material and/or energy cost. Another adverse effect might also be the fact that it would cause the production processes to run slower to ensure prescribed bond formation, thus again leading to process inefficiency and increase production costs. In a preferred embodiment of this invention an improved attachment method is provided which overcomes the problems mentioned above which is specifically advantageous to manufacture the substantially cellulose free absorbent structures having internal fluid management and external liquid management.

The preferred embodiment according to the present invention has resulted from a realization that an attachment between a carrier material and an auxiliary material in the presence of an particulate material can be made more efficiently and effectively if the attachment area where both materials are to be joined is made substantially or at least partially free from said particulate material. There are various ways of preventing or at least minimizing the particulate material from migrating or moving to the attachment areas in between the carrier layer and the auxiliary layer during the attachment process. If the characteristics of the particulate material would allow, one could for instance use electro-magnetic or electro-static forces to pull the intermediate absorbent material away from the attachment area. Also gravitational forces can be used to allow the particulate materials to 'fall away' from the attachment areas at the moment of attachment by way of for instance creating respective higher and lower regions supporting the flow of intermediate absorbent materials in between these regions. Also several purely mechanical ways of cleaning the attachment area by means of friction, scraping or pushing actions such as for instance brushes, scrapers or plungers can be used. However, for some high-speed and minute applications, a still more convenient process is required. After thorough research and testing, the inventor has discovered that a very efficient way to solve the problem is by way of working with airflows. These airflows operate to evacuate the intermediate material away from the attachment area by blowing and/or sucking actions.

An attachment process according to a preferred embodiment of the present invention comprises an airflow generated by blowing zones having an overpressure in comparison to standard process pressure or by suction zones having an underpressure in comparison to standard process pressure. Alternatively, a combination of blowing and/or suction holes can be used to generate such airflow. An airflow moves from a zone of higher pressure towards a zone of lower pressure. For the sake of simplicity, one will use the common and easily understandable wordings 'blowing' and 'sucking' although it should be understood that both are essentially the same as they create the same pressure difference. Unless specifically stated, an airflow from point A to B caused by a blowing zone A with a higher pressure than standard process pressure will be equivalent and can be replaced by an airflow generated by a suction zone B with a lower pressure than standard process pressure.

Generally speaking as soon as the attachment area is made at least partially free from the particulate material, the attachment can be made according to the conventional attachment techniques know in the art such as but not limited to heat and/or pressure sensitive adhesives such as hot-melts, cold-melts, heat activated adhesives, thermoplastic materials, chemical activated adhesives/solvents, curable materials and the like, where the adhesives create the bond between both materials, others involve thermo-mechanical methods such as heat-sealing processes or ultrasonic sealing processes where energy transfer partially melts both materials into each other. Preferably such fusing processes are used as opposed to attachment media.

In order not to complicate the description of the invention but without limiting its scope, one will describe as if the medium in which the process works is a gas e.g. like the air in a normal working environment in a manufacturing plant, and that the standard process pressure is atmospheric pressure. However, it is obvious that the invention can be used within any type of fluid, also when the medium is a liquid. So for the description of this invention, the term 'airflow' will be used as being synonymous for a flow of fluid, meaning both a flow of gas, as well as a flow of liquid. It is also obvious that standard process pressure should not necessarily be atmospheric pressure and that overpressure and under pressure will then just denominate a pressure higher or respectively lower than the reference process pressure.

With reference to FIGS. 1A-D, 2 and 3, an absorbent structure 14 is illustrated made by a method and apparatus according to the invention includes at least one carrier layer 101 and at least one auxiliary layer 102 and absorbent material 110. The carrier layer 101 and auxiliary layer 102 are joined via secondary attachments 115 and preferably also via primary attachments 111. Apart from the primary attachments 111 and secondary attachments 115, there are also unattached regions 119, where there is substantially no attachment, bond and/or joint between the carrier layer 101 and auxiliary layer 102, thereby providing pockets 130 in which the absorbent material 110 can be located to form well-designed clusters. The primary attachments 111 correspond with a primary attachment grid, whereas the secondary attachments 115 correspond with a secondary attachment pattern. As the secondary attachment pattern will release under the swelling force of the absorbent materials and/or under the influence of water, the secondary attachment 115 should have a relative low separation force is use. The primary attachment grids will preferably be kept substantially intact.

As carrier layer 101 and/or auxiliary layer 102, having a typical basis weight in the range of 3-400 gsm, one can choose from a variety of materials such as but not limited to high-lofts, airlaids, rigid, stretchable or elastic non-wovens or a woven fabric, wetlaid material such as cellulose tissue, paper, film, tissue, perforated films, foam material, thermoplastic material, layers of adhesive or whatever material suitable within the absorbent structure 14. The sandwich layers can be made out of the same or different materials having different compositions, weights and/or structures. In a preferred embodiment, at least one of the layers is liquid permeable over at least part of its surface so that liquids can be taken up in the Z-direction. In an alternative embodiment of the present invention the absorbent structure 14 comprises an additional distribution layer which helps to additionally absorb, distribute and transport liquids and having a capability to disperse the liquid permeating within said distribution layer from the less absorbent area's (e.g. saturated) to the more absorbent area's (e.g. unsaturated). In yet another alternative embodiment of the present invention the absorbent structure 14 comprises an additional liquid-impermeable, either hydrophilic or hydrophobic, wicking layer which helps to wick, distribute and transport liquids and having a capability to disperse the liquid over the surface of said wicking layer from the less absorbent area's (e.g. saturated) to the more absorbent area's (e.g. unsaturated).

Figure 1B:
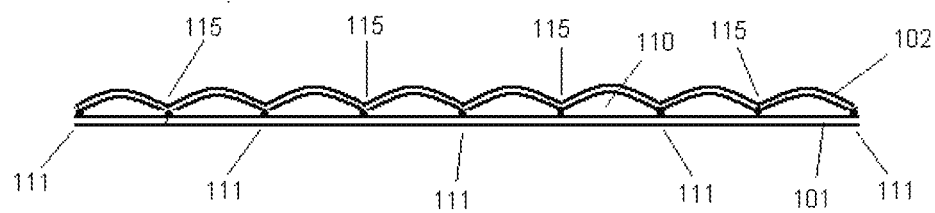
Figure 1C:
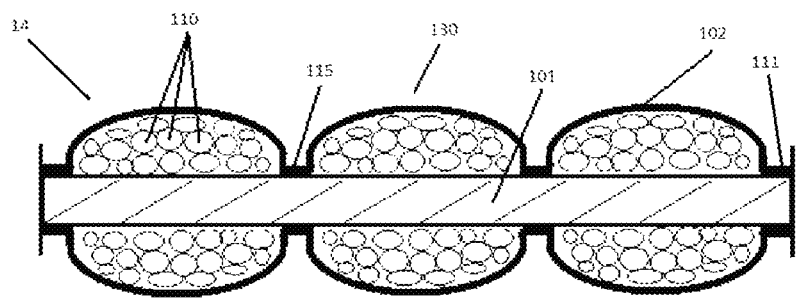
Figure 1D:
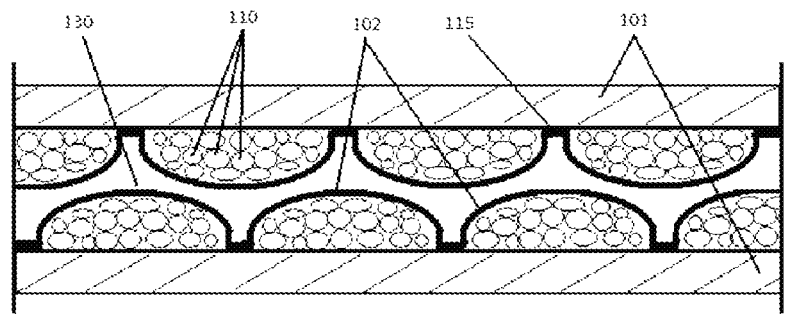
Figure 2:
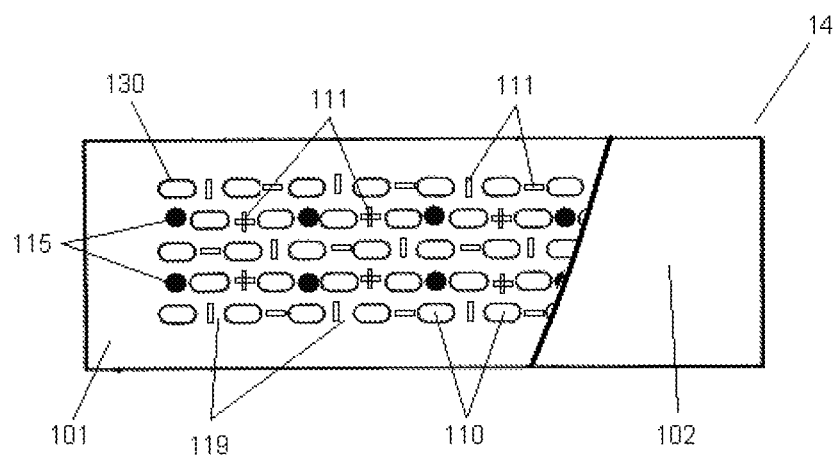
FIG. 2 provides a top view schematic illustration of an absorbent structure made according to an embodiment of the invention.
Figure 10:
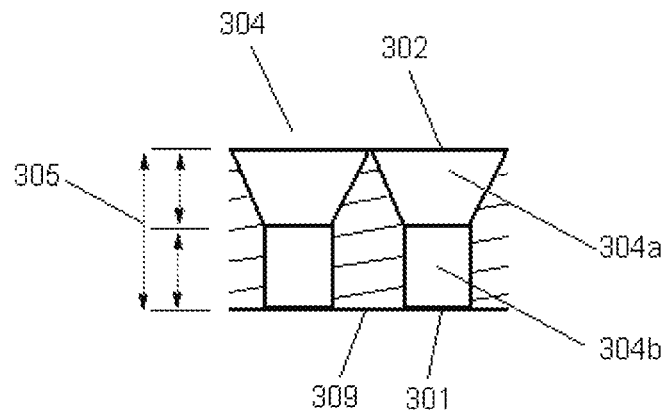
FIG. 10 provides a cross-sectional schematic illustration of a clustering means according to an embodiment of the present invention.

Referring to FIG. 1B, the carrier layer 101 is covered on one side by discrete amounts of absorbent material 110, which is covered by an auxiliary layer 102. The auxiliary layer 102 lies on top of the absorbent material 110 and is joined to the carrier layer 101 thereby providing pockets 130 holding the absorbent material 110. Referring to FIG. 10, it has been found that absorbent structures 14 can be formed by combining two layers of absorbent material 110. The absorbent structure 14 comprises one carrier layer 101, two layers of absorbent material 110 and two auxiliary layers 102. Referring to FIG. 1D, the combined absorbent structure 14 as shown comprises two layers of absorbent material 110, two carrier layers 101, and two auxiliary layers 102. When two storage layers are joined, this is preferably done such that the first carrier layer 101 of the first storage layer faces the auxiliary layer 102 of the second storage layer, while the auxiliary layer 102 from upper storage layer is situated on the wearer facing surface and the carrier layer 102 from lower storage layer is situated on the garment facing surface of the sandwiched composite.

Figure 3:
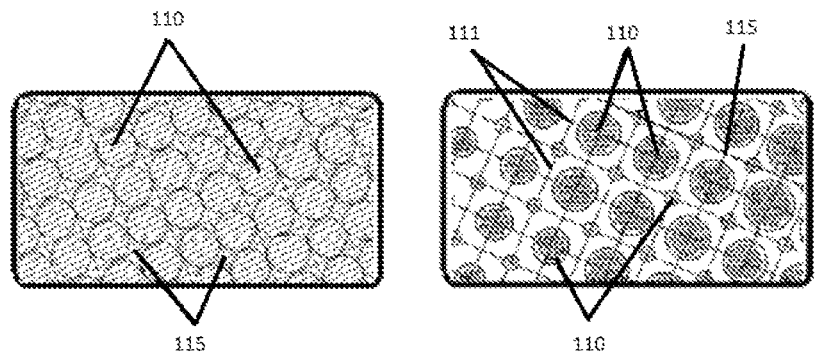
FIG. 3 provides a top view schematic illustration of differently located and sized clusters of absorbent material obtainable according to an embodiment of the invention.
Figure 4:
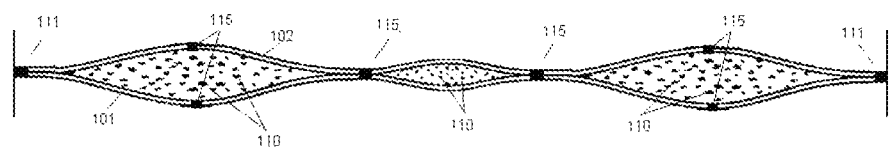
FIG. 4 provides a top view schematic illustration of an absorbent structure in a partially wetted state made according to an embodiment of the invention, indicating substantial permanent primary attachments; and the gradual release by the still joined and already loosened temporary secondary attachments.
Figure 5:
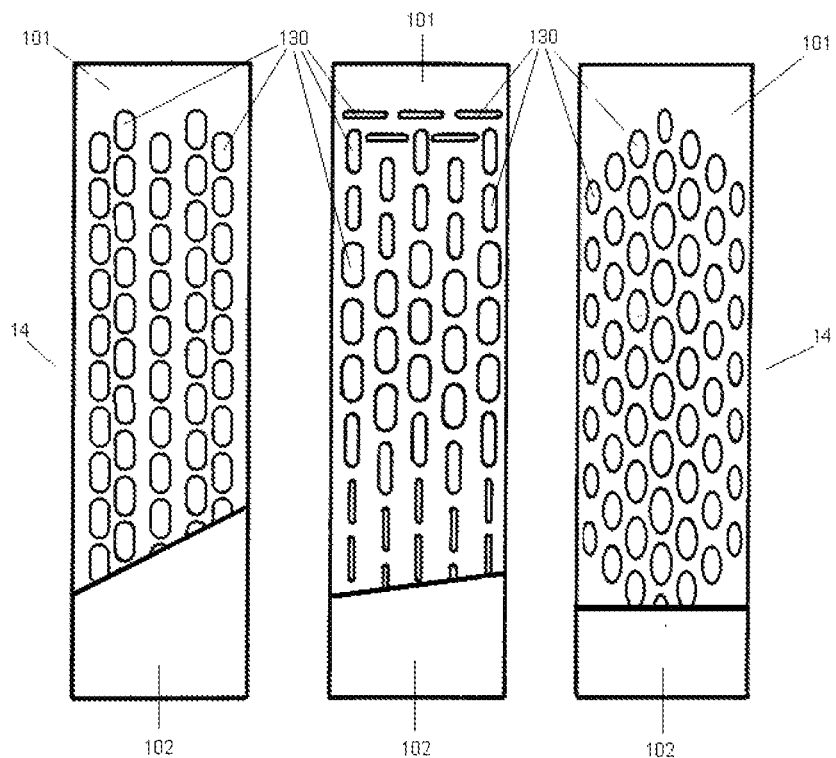
FIG. 5 provides top view schematic illustrations of an absorbent structure made according to an embodiment of the invention indicating different cluster patterns.
Figure 5:
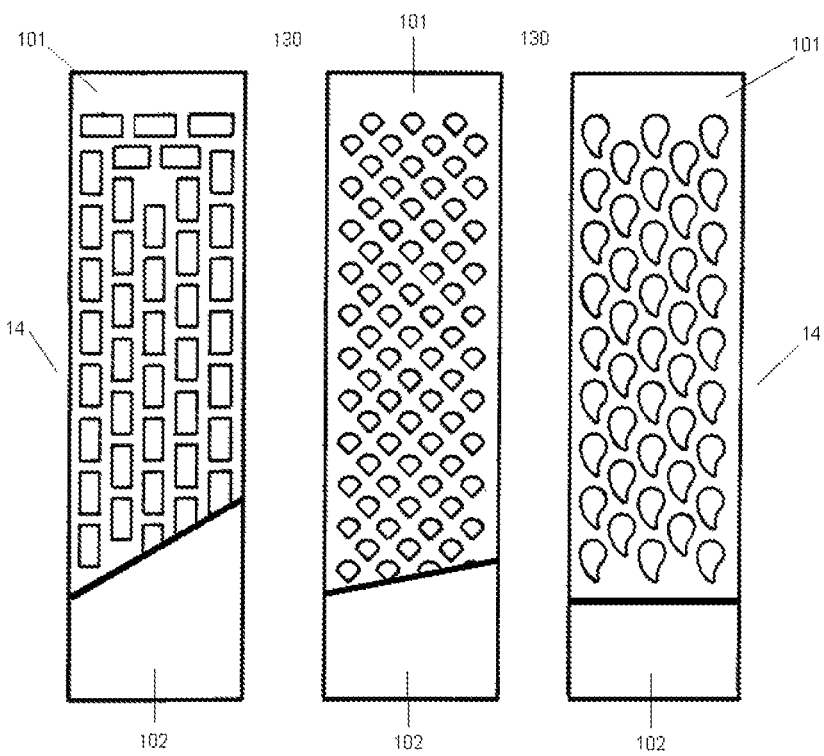

As can be seen from FIGS. 3 and 5, the absorbent material pattern formed in between attachments can be random or regular, substantially continuously connected or isolated, fully-covering or partially covering and/or any other suitable combination. Preferably the absorbent material regions consists of several clusters of absorbent material 110, surrounded by areas where substantially no absorbent material 110 is present, which can act as additional distribution and transport channels facilitating the flow of liquid away from the point of insult and towards available clusters of absorbent material 110. Weight distribution of absorbent material 110 over the absorbent structure 14 can be regular across the major surface or can profiled, i.e. the basis weight of the absorbent material 110 may change depending on its position in the absorbent structure 14, for instance very desirable for use in diaper and pants cores where one would like to concentrate absolute and/or relative more absorbent material 110 near the point of liquid insult. Suitable materials such as for instance highly permeable SAP are offered by Evonik, BASF and Nippon Shokubai. Although preferably the absorbent polymer material form up to 100% of the absorbent material 110 it can also be used in combination with other materials such as for instance cellulose fibres or fluff pulp, however preferably the amount of fibrous materials would not make up more than about zero to 40 weight percent. Fully cellulose free structures benefit maximally from this invention.

Typical examples of methods used to join material and layers to each other are by way of example, but are not limited to, the use of an adhesive such as for instance pressure sensitive adhesive, curing, chemical links such as for instance hydrogen and covalent bonds or via the use of ultrasonic and/or other thermal, mechanical or thermo-mechanical attachment techniques such as for instance heat sealing, needling, air, entanglement, resistance and water jet pressure, and the like.

It is also preferred to design the attachments so that they have an average surface size of at least about 0.5 mm$^2$, preferably at least about 1.0 mm$^2$, 2 mm$^2$ or 3 mm$^2$, more preferably at least about 16 mm². Also the density of the attachments can vary, depending on the surface size of the individual attachments and desired separation forces. For attachments with a surface area smaller than 1 cm² for instance, it is recommended to use a density of at least about 100 per m². In another embodiment of this invention, the primary attachments 111 are arranged in a primary attachment grid composed of continuous lines so as to allow for additional liquid distribution and transport, for a high separation force and high resistance against the propagation of an eventual cracks or fissures in the pockets 130. The primary attachment pattern is carefully designed so that in a wetted state, the swollen material remains stabilized around the locations where it was restrained and/or immobilized in dry state. Failure to do so would result in breaking-up and/or displacement of the wet absorbent material, resulting in defective fluid management and to loss of performance, reduced fit and comfort, even full failure. The primary attachment pattern also accommodates the liquid management surface structures. The breaking of the secondary attachments 115 allows the carrier layer 101 and/or auxiliary layer 102 to deform, stretch and change shape. As a result, the minimal volume pockets are able to expand to an intermediate volumes and finally to maximum volume compartments so as to accommodate the extra volume resulting from the highly expandable absorbent material 110. Thus, an absorbent structure 14 with expandable pockets with additional activated free swell volume is created, allowing the absorbent material 110 to be more effectively and efficiently used and reducing the risk of bursting of one or more sandwiching layers. The extra volume created by the expanding pockets can for instance be about 1% to 5% of the original volume. Preferably it is higher than about 5% to 25%, more preferably higher than about 25% to 50%, most preferably higher than about 50% or 100% of the original volume. In an alternative embodiment, the absorbent structure 14 consists of multilayered sandwich structures where on the first sandwich structures, whereby the additional layers of absorbent material and/or complementary layers provide further liquid absorption performance whilst retaining good product integrity, both in a dry and wet state.

In an absorbent structure made by an embodiment of the invention secondary attachment 115 consist of weaker secondary attachments and stronger secondary attachments where weaker secondary attachments loosen faster than the stronger secondary attachments. The different functionalities in between the primary attachments 111 and secondary attachments 115 in combination with the bonding strength differentiation in between weaker secondary attachments and stronger secondary attachments allows the design of an absorbent structure 14 with a predetermined, controlled and/or phased volume-expansion of the absorbent structure for ultimate fluid management.

Figure 6:
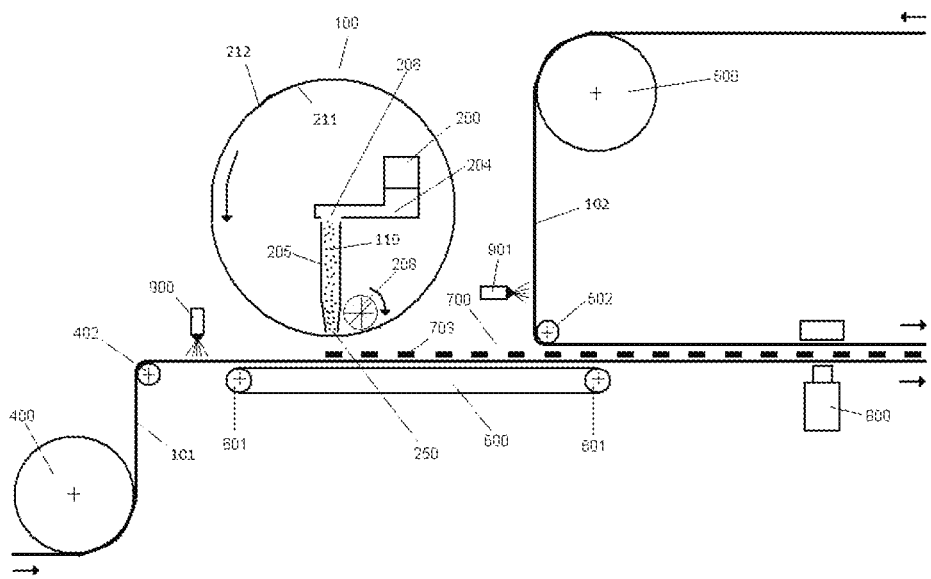
FIG. 6 provides a schematic process diagram for carrying out the invention.

With reference to FIG. 6, the present invention provides a method and apparatus for forming a composite structure 700 having a plurality of discrete particulate material clusters which are preferably deposited on a carrier layer 401 and contain selected quantities of particulate material 201. The representatively shown apparatus includes a clustering means 250 with perforations 304, and a particulate material supplying means 200 for providing particulate materials 201 towards the clustering means 250. A web supplying means 400 provides a carrier material 401 and a support means 600 moves the carrier material 401 adjacent the clustering means 250, the clustering means 250 preferably provided in the form of a substantially endless rotating drum 100.

The clustering means 250 includes a pattern of perforations 304, preferably in the form inlet regions 304a joined to outlet regions 304b, and are arranged to form and provide a desired printing pattern 320 of particulate material clusters 703 onto the carrier layer 401. The support means 600 is preferably in substantial contact with the support surface 412 of the carrier material 401. The support means 600 preferably ensures a close enough connection in between the deposit surface 411 of the carrier material 401 and the outlets regions 304b to prevent unwanted migration of the particulate materials 201 from the carrier deposit zones 415 to the carrier inter-deposit zones 416. Although not required to work the current invention, it is highly recommended to foresee a close pressure contact connection in between the deposit surface 411 of the carrier material 401 and the outlets regions 304b and inter-outlet zones 309 of the clustering means 250 to prevent unwanted migration and/or shifting of the particulate materials 201 from the carrier deposit zones 415 towards the carrier inter-deposit zones 416. The close deposit contact ensures favourable deposit and printing of particulate material 201 onto the deposit surface 411 of the carrier layer 401 without substantially loss of material.

The resultant printing pattern 320 forms desired and substantially spaced-apart particulate material clusters 703, preferable without any substantial amounts of particulate materials 201 in between the particulate material clusters 703. Preferably an additional positioning step is foreseen by way of a providing position means, to stabilize, position and/or reposition the particulate material clusters 703 in their exact positioning or pocketing pattern 420 before immobilising it in the composite structure. The depositing or printing pattern 320 provided by the clustering means 250 can but does not necessarily have to correspond with the positioning or pocketing pattern 420 formed by the positioning means. For instance relative homogenous, wide or blurry depositing patterns 320 will preferably not correspond with the discretely clustered positioning patterns 420 required in case particulate material such as absorbent particulate polymer material is to pocketed and immobilised by means of primary and/or secondary attachments made by means of ultrasonic bonding to make substantially cellulose free absorbent structure for use in an absorbent article such as a baby diaper or pants.

A covering means 500 provides an auxiliary material 501, such as for instance a liquid-permeable fibrous web such as a non-woven, paper, tissue, woven, fabric, web, perforated film or foil and the like to sandwich said particulate material clusters 703, preferably comprising large amounts of absorbent polymer material, between the carrier material 401 and auxiliary material 501. Alternatively, not preferably however, the auxiliary material 501 can also represent a homogenous and/or heterogeneous layer of glue, adhesive, binders, resins, thermoplastic material and the like, capable of sandwiching the particulate materials clusters 703 between the carrier material 401 and auxiliary layer 402. This relative expensive, technically challenging and environmentally burdensome alternative embodiment according to the invention is not preferred above the typical non-woven, paper or tissue layers for instance.

The clustering means 250 is suitably constructed and arranged to direct a selected flow of particulate material 201 onto the carrier deposit zones 415 of the carrier layer 401. It should be appreciated that other particulate material 201 may also be introduced via the clustering means 250 as desired. A particulate supplying means 200, such as for instance a K-Tron weight and loss feeder, Model N° K10s, type of particulate delivery system can be configured to deliver required amounts of particulate material 201 through a feeding tube 205 into the clustering means 250. The particulate material 201 reach the perforations 304 by means of gravity and/or other physical forces. In particular embodiments, a conventional air-conveying system may be employed to move and guide the particulate material 201 and resultant particulate material stream to the desired locations in the clustering means 250. Alternatively such forces may for instance be electro-magnetic or electro-static forces in case the particulate material 201 is responsive to a magnetic field or electro-charges, and magnets or charging devices are placed to guide the particles towards the perforations 304. Alternatively, the particulate material 201 can, for instance, be gravimetric or volumetric assessed, guided and fed indirectly via the feeding tube 205 and/or directly into the clustering means 250 under the influence of gravity without the use of additional conveying air.

Optionally, one can also provide a vacuum suction system in function of the deposit zones 415 of the carrier material 401, creating an air flow towards the perforations 304 and/or deposit zones 415. Such vacuum suction system would generate suitable levels of vacuum within an appointed vacuum section, and would provide a desired level of vacuum within the clustering means 250. It should be readily appreciated that such particular levels of vacuum generated within clustering means 250 and/or drum 100 would depend upon the individual circumstances of the manufacturing line. For example, at higher rates of rotation of the drum 100, relatively higher levels of vacuum may be required within clustering means 250. In addition, the use of conveying means to transport the particulate material 201 into the clustering means 250 may necessitate the use of even higher levels of vacuum. It should also be readily appreciated that the levels of vacuum shall also depend upon the porosity of the carrier material 401, and the usage of possible carrier material 401 would for instance be limited to fibrous web materials and/or perforated films and foils. For the reason above and in light high energy consumption this vacuum suction usage is an alternative embodiment according to the invention, however not one of the most preferred one. The positioning means can be mounted on such vacuum suctions systems in light of the preferred pocketing pattern 420 or can alternatively be unitary.

More economically and environmentally beneficial production processes with lower energy usage and more freedom on the choice of carrier material 401 are preferred. Further to extensive testing it was however demonstrated that using gravity will be sufficient for a wide range of particulate material 201 usages at various production speeds.

The particulate material 201 supplied via the particulate material supplying means 200 is preferably provided in uniform particulate material stream, reaching a width equal to or slightly greater than the width 310 of the perforation pattern 300 on the side of the inlet regions 304a. In order to improve uniformity, a vibrating supply means 200 might be used. In a preferred embodiment, a feeding tube 205, with a proximal opening 206 and distal opening 207 can be used to concentrate the particle material stream onto a certain area. Such feeding tube 205 may have various suitable longitudinal and transversal shapes and is preferably designed in light of the dimension and shape of the clustering means 250, its perforation pattern 300, its perforations 304 and the desired printing pattern 320. The feeding tube 205 may also converge towards the clustering means 250 to effectively and efficiently guide the particulate material stream to the inlet regions 304a. The particle supply means 200 preferably contains a continuous supply and a dosing system 204 of a gravimetric, volumetric or other type so as to control the quantity and quality of particles fed into the perforations 304. Such particle supply means are being offered by Acrison, Inc., having offices in New Jersey, New York.

The particle material 201 such as absorbent polymer material, more preferably absorbent particulate polymer material may be provided and used in various shapes or forms, such as granular, spherical, flakes, fibrous, and will often consist of irregularly shaped particles, having a mean particle size from about 10 µm to 1000 µm, preferably with less than about 5% by weight having a particle size of 5 µm, and preferably with less than about 5% by weight having a particle size of more than about 1200 µm. For use in absorbent structures to be used in absorbent articles, an absorbent material will be selected which can swell upon contact with liquids, such as bodily exudates. Such materials can be supplied in a granular form by Evonik from Essen, Germany, BASF from Antwerp, Belgium, Nippon Shokubai from Osaka, Japan and San-Dia from Tokyo, Japan. These are cross-linked polymeric materials that can absorb at least about 5 times their weight of an aqueous 0.9% saline solution as measured using the Centrifuge Retention Capacity test (Edana 441.2-01).

The web supplying means 400 can include any conventional spindle and supply roll controlling mechanism of the type that is know in the art. For example, suitable spindle and control mechanisms are available from Martin Automatic, company with offices in Rockford, Ill.

The carrier material 401 may preferably be brought in their desired position via guiding systems 402 and the auxiliary material 501 may preferably be brought in their desired position via the guiding systems 502, and the support means 600 is preferably controllably strained via tensioning means 603 and operated via guiding means 601 and 602. The composite material 700 is preferably guided via guiding means 603 and the desired material 702 is preferably guided by guiding means 604.

The carrier material 401 can be any suitable material web which has sufficient strength to process through the apparatus, and preferably economically, environmentally and usage sensible. The carrier material 401 may comprise a paper or fibrous tissue, woven or non-woven fabric, a cellulose web or batt, airlaid or wet laid structure or the like. Alternatively, the carrier material 401 is a porous, gas permeable web material such as a porous film or fibrous web.

The auxiliary material 501 can be any suitable material web which has sufficient strength to process through the apparatus, and preferably economically, environmentally and usage sensible. The carrier material 401 may comprise a paper or fibrous tissue, woven or non-woven fabric, a cellulose web or batt, airlaid or wet laid structure or the like. Alternatively, the carrier material 401 is a porous, gas permeable web material such as a porous film or fibrous web. Furthermore the auxiliary material 501 can also represent for instance a spray, film and/or layer of glue, adhesive, binders, resins, thermoplastic material and the like together with the carrier material 401 capable of sandwiching the particulate material clusters 703.

The carrier material 401 and/or auxiliary material 501 may also be an essentially endless web material in the longitudinal direction. One preferred web material is a so called SMS material, comprising a spunbonded, a meltblown and a further spunbonded layer. Highly preferred are permanently hydrophilic non-wovens, and in particular non-wovens with durably hydrophilic coatings. An alternative preferred material comprises a SMMS-structure. Another preferred web material is a nonwoven containing cellulosic fibers, paper or tissue sheet or other airlaid, drylaid or wetlaid material, as these products greatly improve the wicking capacity of the product. The carrier and auxiliary materials 401 and 501 may be provided from two or more separate sheets of materials or they may be alternatively provided from a unitary sheet of material. Preferred nonwoven materials are provided from synthetic fibers, such as PE, PET and most preferably PP. As the polymers used for non-woven production are inherently hydrophobic, they are preferably coated with hydrophilic coatings.

The clustering means 250 can preferably be mounted onto a or unitary with a drum 100 having perforations 304 arranged in a perforation pattern 300 along its circumferential- and/or width-wise direction and thus directly or indirectly piercing or perforating the drum 100 in the radial direction, from its inner surface 101 to its outer surface 102. Alternatively, according to another embodiment of the invention, the clustering means 250 are replaceably mounted and/or unitary incorporated on a substantially endless belt carried on a system of transporting rollers. Suitable forming belt systems are available from Paper Converting Machine Company, a business having offices located in Green Bay, Wis. Driving means, such as conventional electric motors or the like, are constructed and arranged to rotate or otherwise move and translate the clustering means 250 at a predetermined surface speed along a desired manufacturing direction and speed. Various configurations can provide the desired composite structures while operating at high surface speeds of at least about 0.5 m/sec, preferably at least about 1 m/sec, more preferably at least about 3 m/sec and most preferably more than 7 m/sec.

The carrier material 401 is delivered onto or adjacent the outer peripheral surface of the clustering means 250 mounted onto or unitary with drum 100. As the drum 100 rotates, the moving surface of the drum 100 transports the clustering means 250 and the support means 600 guides the carrier material 401 in close proximity and past the clustering means 250 in light of the intended deposit of particulate material clusters onto the deposit surface 415 of the carrier layer 401. For the sake of simplicity, the wording 'drum' is used, denominating an essentially round circumference, but it is clear to the person skilled in the art that any type of endless body, provided with the desired perforation pattern 300 can be used. The surface of such body can be rigid such as in perforated aluminum plates, or soft such as in a belt. Preferably, a drum 100 made out of steel frame with reinforced aluminum plates will be used.

Figure 7:
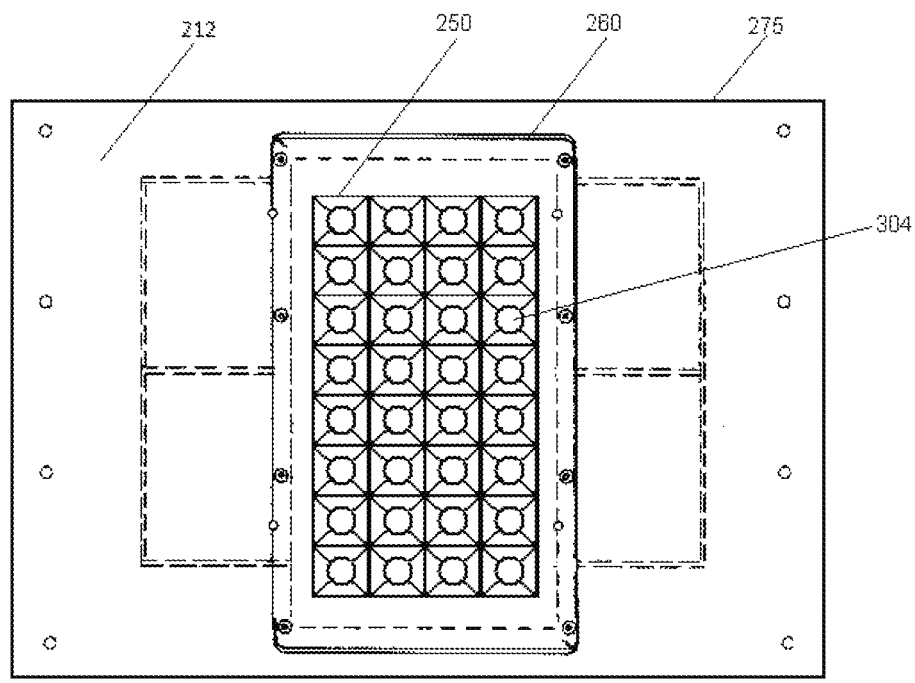
FIG. 7 provides a schematic top view illustration of a clustering means mounted onto a drum according to an embodiment of the invention.

With reference to FIG. 7, in a preferred embodiment according to the invention the outer surface 202 of the drum 100 can be operationally divided into a series of predetermined article segments 275. Each article segment 275 mounted and incorporated into the drum 100 generally corresponds to an absorbent structure 14 for placement in a single absorbent article. The outer surface 202 of the drum can further comprise a plurality of plate means 260 which comprise the clustering means 250 and are serially positioned and longitudinally spaced along the circumference of the drum 100 so as to provide a series of mountable clustering means 250 able to deposit the particulate material 201 on the carrier material 401. Preferably the article segment 275, the plate means 260 and clustering means 250 are designed so as to complement the rounded drum 100. The different sections making up the drum 100 are constructed of a material, such as metal, that is sufficiently strong to withstand the forces and stresses encountered during operation.

Figure 8:
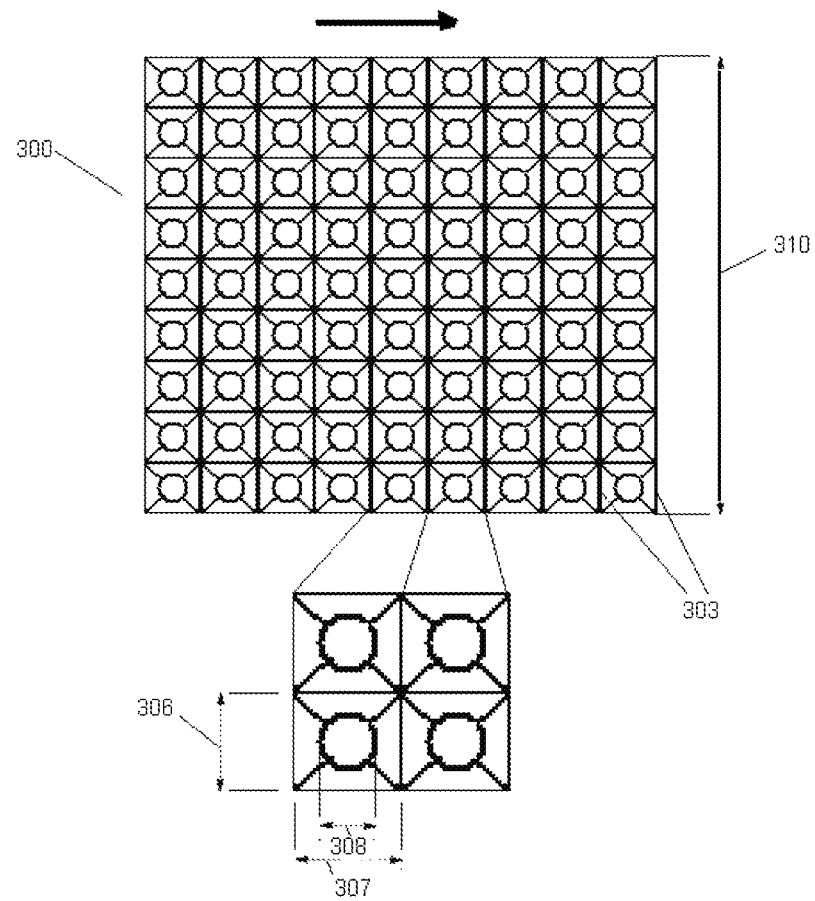
FIG. 8 provides a schematic top view illustration of a clustering means according to an embodiment of the invention.

The perforations 304 can have a variety of shapes including, but not limited to, circular, oval, square, rectangular, triangular, and the like. The perforation pattern 300 shown in FIG. 8 is a square grid with regular spacing and size of circular perforations 304. Other perforation patterns 300 can be hexagonal, rhombic, orthorhombic, parallelogram, triangular, rectangular, and any and all combinations and derivations thereof. Alternatively, using an irregular perforation pattern 300 with varying sizes and shapes of the perforations 304, very specific and/or complex resultant printing patterns 320 can be made. The spacing between the grid lines 303 may be regular or irregular. Alternatively the configurations of the perforation 304 can also be arranged with one or more elongate shapes positioned with their relatively longer axes aligned at selected angles which diverge or converge to the centerline of the perforation pattern 300. The desired perforation 304, and their respective inlet region 304a and outlet region 304b volumes, are furthermore formed by height 305 of the individual clustering means 250.

Figure 9:
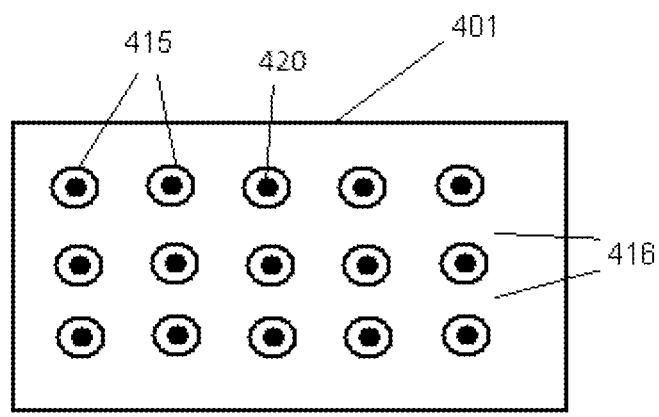
FIG. 9 provides schematic top view illustration of a carrier layer with deposited patterns and positioning patterns according to an embodiment of the invention.

With reference to FIG. 9, the perforation patterns 300 will determine the depositing patterns 415, whereby the particulate materials 201 will preferably be deposited in the carrier deposit zones 415 on the carrier material 401 and preferably not onto the carrier inter-deposit zones 416. In a preferred embodiment the additional positioning means provides for the (re)positioning of the depositing pattern 415 to their final pocketing pattern 420. This is especially advantageous in case of homogenous or heterogeneous particulate material depositing, but is also greatly preferred to focus the particulate materials 201 from their depositing pattern 415 and from the inter-deposit zones 416 to exact pocketing pattern 420, before immobilising them by creating for instance primary and secondary attachments in between the carrier material 401 and the auxiliary material 402.

With reference to FIG. 10, clustering means 250 includes a pattern of perforations 304 separated from one another by inter-perforation zones, being preferably inter-inlet ridges 303 on the feeding side of the clustering means 250 and inter-outlet zones 309 on the deposit side of the clustering means 250. The perforations 304 have a top opening 302, corresponding to the inner surface 211 of the drum, a bottom opening 301, corresponding to the outer surface 212 of the drum, and a height 305. Top opening 302 and bottom opening 301 can vary in size and shape from each other, where the top opening 302 is in this instance rectangular with transversal side 306 and longitudinal side 307 and the bottom opening 301 is in this instance circular with diameter 308. In a preferred embodiment, the top opening 302 is larger than the bottom opening 301, thus creating a converging funnel structure in the inlet region 304a, allowing the efficient collection of particle material 201 which slides easily into the outlet region 304b. In a preferred embodiment, the top opening 302 are designed as such that the inter-inlet ridges 303 between adjacent top openings 302 are very sharp and narrow so that substantially no particulate material 201 can remain and/or pile up on these inter-inlet ridges 303 and thus substantially all particulate material 201 is collected by the perforation 304.

If the perforations 304 are overfilled, i.e. if more particulate material 201 is present than the perforations 304 can take or than can instantaneously be evacuated via the perforations 304, one has 'overfill'. Particulate material 201 will then accumulate and rise until above the level of the top opening 302 of the perforation 304. In that case, a sweeping means 208 will level the surface of the particulate material 201 with that of the inner surface 213 of the drum 100 and thus remove the excess particulate material 201 so that only a volume of particulate material 201 essentially corresponding to the volume of the perforation 304 is being transferred to the carrier material 401 during depositing. The sweeping means 208 can be for instance a scraper bar made out of durable material, or, as depicted in FIG. 6, a rotating brush or wheel 208 mounted closely above the inner surface 213 of the drum 100, or any other suitable solution fit for the purpose. Such sweeping 208 means will also evacuate any particulate material 201 present on the ridges 303 between the adjacent top openings 302. If the perforations 304 are under-filled, i.e. in case the particulate material supply means 200 feeds less particulate material 201 (by volume) into the perforations 304 of the clustering means 250 than can be evacuated during the depositing process, one has 'under-fill'. This is preferred in application, especially where it is important to have the correct weight of particulate material 201, rather than working via the volume of the particulate material 201.

As explained above, the overfilling method functions with sweeping means can act as a volumetric dosing system, where the prescribed volumes, dimensions and shapes of the perforations 304 act as the volumetric dosing and printing space and gives excellent results if the particulate material 201 is very homogeneous in density and particle size, or if the weight of the dosed particles is less relevant than their volume.

However, in many cases it is required to dose the correct weight, rather than the corresponding volume. Such particulate material 201 often have irregular densities by nature and/or such irregular densities are often aggravated by handling and transportation whose vibrations cause the particulate material 201 to segregate, bringing the lower density particles on top and the higher density particles below. Using a volumetric method could then result in important weight differences from one product to another which is undesirable, making gravimetric dosing preferably.

Carrier material 401 which is delivered by the web supplying means 400 onto the support means 600 delivers the carrier material 401 in close proximity of and preferably against the outer periphery of the clustering means 250. If the clustering means 250 and the carrier material 401 are pressed to one another they tightly seal off the outlet regions 304b and when preferably moving at essentially zero speed difference to one another, the particulate materials 201 fed by the supply means 200, preferably guided via feeding tube 250, are able to be continuously and controllably deposited onto the clustering means 250 into the perforation 304 via the inlet regions 304a thereby creating the particulate material printing pattern 320 on the deposit zones 415 of the carrier material 401. Preferably the printing pattern 320 is treated via positioning means so as to reposition the particulate materials 201 into the pocketing pattern 420. Optionally, the particulate material clusters 703 are immobilised, bond, joined and/or otherwise secured restrained in relation to the carrier layer via any suitable means, such as for instance glue, binder, sprays, films, network, webs, etc.

Due to the gravity or other forces, the particulate material 201 will exit the perforations 304 via their bottom opening 301, thereby providing the desired printing pattern 320. This desired printing pattern 320 is substantially retained when the drum 100 separates from the carrier material 401. In the absence of a relative close seal in between the outer surface of the clustering means 250 and the deposit surface 411 of the carrier material 401, a gap 103 will create a possible blurring effect of the desired printing pattern 320, since the drum 100 and carrier layer 401 move at significant speeds and allow migration of the particulate materials 201. Therefore it is recommended to keep the gap 103 a small as technically acceptable.

However, even with a very small gap 103, it is obvious to the person skilled in the art that, depending on the nature of the particulate material 201 and on the amount of particulate material 201 one wants to deposit via one single perforation 304, the actual resulting printing pattern 320 might differ slightly from the perforations pattern 300. The effect is caused by gravity which might pull the particulate material clusters 703 apart so that the particulate material footprint 705 on the carrier layer 401 is wider and/or larger than the bottom opening 301 of the perforations 304 and the forces of inertia might further distort the printing pattern 320 in the direction of the web movement, thereby creating a skewed image 704. The additional positioning means are used to overcome this disadvantageous blurring effect completely and focus all particulate material 201 in their pocketing pattern 420.

Figure 11:
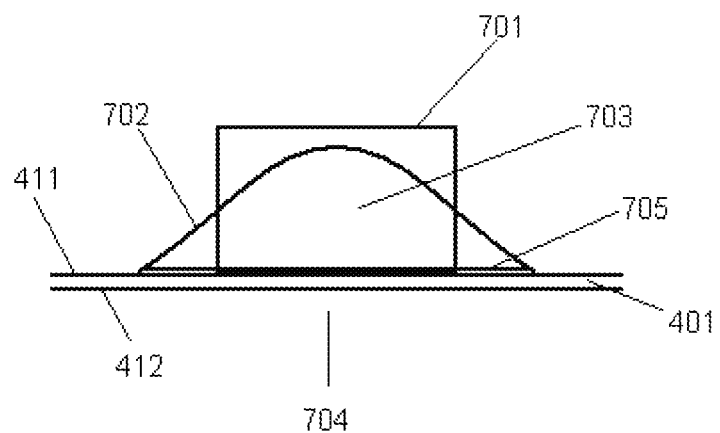
FIG. 11 provides a cross-sectional schematic illustration of a deposited particulate material cluster according to an embodiment of the present invention.

FIG. 11 illustrated how, due to the various forces mentioned above, for a set of printed particulate material clusters 703, the printed shape 702 might differ from the original shape 701 which the particulate materials 201 had while still caught in the perforation 304 of the clustering means 250 before being deposited on the carrier layer 401. A careful design of sizes, locations and shapes of the perforations 304 and related dimensions, shapes and rotating speed of the clustering means 250 and drum 100 will ensure satisfying results after having evacuated the particulate material 201 onto the carrier material 401.

The composite structure 700 as a combination of the carrier material 401 and the particulate material clusters 703 is moved away from said clustering means 250 via a transport means, while in case required a positioning means ensures the particulate material clusters 703 are not unacceptably distorted, the particulate materials 201 do not unintentionally migrate to the inter-deposit zones 416 and/or are lost or wasted due for instance high machine speeds, air and material flows, gravitational and other forces and the like. In a preferred embodiment the composite structure 700 is immediately stabilised when taken over from the carrier material support means 600 by the positioning means being for instance opposing contact pressured longitudinal conveyer belts, vacuum suction means, or the like. The support means 600 or other transport means can be unitary with positioning means.

More preferably one can also immediate bond or join a second web material such as for instance an auxiliary material 501 directly or indirectly unto the carrier material 401 and the particulate material clusters 703 deposited thereon according to printing pattern 320, so that the particulate materials 201 are sandwiched, immobilized, bonded, joined and/or restrained in between the carrier material 401 and auxiliary material 501 in their desired location and shapes by means of the thereby formed pockets. The auxiliary material 501 can represent various known alternatives and techniques of immobilization, bonding, joining and/or restraining means, such as for example homogenous and/or heterogeneous patterns, shapes, lines, sprays, coatings and/or films of for instance glues, binders, resins, plastics, adhesives, curing agents, heat activated and heat sealing adhesive, pressure sensitive adhesive and the like.

The shape of these positioning means can have a variety of shapes including, but not limited to, circular, oval, square, rectangular, triangular, and the like. The positioning pattern 420 of the positioning means is preferably a grid with regular spacing and size of circular or rectangular recessions and/or elevations. Other shapes can be hexagonal, rhombic, orthorhombic, parallelogram, triangular, rectangular, and any and all combinations and derivations thereof. Alternatively, using an irregular positioning pattern with varying sizes and shapes, very specific and/or complex resultant positioning patterns can also be made. The spacing between the recessions and/or elevations may be regular or irregular. Alternatively the configurations of the positioning means can also be arranged with one or more elongate shapes positioned with their relatively longer axes aligned at selected angles which diverge or converge to the centerline of the positioning pattern 420. The positioning means can be unitary with the attachment means.

As shown in FIG. 6, a first adhesive applicator 900, spraying adhesive onto the carrier material 401 prior to the deposit of the particulate material 201 may be provided. The auxiliary material 501 may also be provided with a second adhesive applicator 901 and the resulting sandwich structure is additionally preferably secured via an ultrasonic attachment means 800.

The first and second adhesive applicator 900 and 901 can be constructed and/or operated so as to provide a multiplicity of overlapping loops of swirled adhesive to hold together the composite web 700. A plurality of adhesive swirl patterns can be selectively overlapped to provide the desired level of bonding and/or joints within the appointed pockets. It should be readily appreciated that other configurations of the adhesive patterns, such as stripes or individual islands of adhesive may be employed to give operable bonding. In addition, it should be readily appreciated that other types of adhesive application systems, such as printing, spraying, extrusion, or the like, may also be employed to generate the desired arrays of patterned adhesive. Alternatively the second adhesive applicator 901 can be placed directly above the composite structure 703 so as to directly spray upon and immobilize, bond, join and/or restrain the particulate materials clusters 703 onto the auxiliary material 401, whereby the sprayed layer of adhesive would form the respective auxiliary material 501. In light of economic, environmental and technical considerations this adhesive immobilization, bonding, joining and/or restraining of the composite structure 700 is however not preferred and only considered an alternative embodiment according to the invention. The adhesive applicators 900 and 901 can be supplied by Nordson, United States, whereas a adhesives can be supplied by Henkel, Germany.

Alternatively the auxiliary material 501 can for instance also comprise a liquid-permeable layer or web material, such as films, foils, tissues, fabrics, webs or the like. The layer may for instance comprise paper, tissue, wetlaids or drylaids, wovens or non-woven and/or may be composed of for instance hydrophilic materials or composed of a hydrophobic material which has been suitably treated to render it sufficiently hydrophilic. An alternative configuration of the auxiliary material 501 can, for example, comprise a cellulosic layer of fluff or wood pulp. The fluff or wood pulp layer may be substantially unbonded, or optionally and preferably provided with the necessary structural and/or functional integrity by the means know in the art (e.g. air jet, water jet, knitting, calendaring, sonic bonding etc.) and/or may include a selected proportion of a bonding agent, such as a resin, adhesive, thermally fusible fiber or the like, which is operably distributed therein. For example, a thermally fusible, thermo-bonding fiber composed of a polyethylene/polypropylene, sheath/core bi-component fiber may also be employed.

Additionally the composite structure 700 and/or absorbent structure 14 can be alternatively and/or complementary be further combined with any and all other suitable covering, absorbency feature enhancing, protective, functional, structural and/or strengthening materials, fabrics and/or webs (e.g. acquisition layer, surge layer, distribution layer, wicking layer, backing layer, elastic layer, colored layer, perfumed layer, lotion layer, informative layer, etc.) etc.

Auxiliary material 501 can preferably be bound or joined to the carrier material 401 with the particulate material clusters 703 immobilized and/or restrained there between via attachment means 800 such as for instance ultra sonic and/or other thermal, mechanical or thermo-mechanical bonding techniques. Such discrete bonds or joints in between the carrier material 401, particulate material clusters 703 and/or auxiliary material 501 can preferably be provided in one or more of the inter-deposit zones 416, more preferably in one of the inter-positioning zones, in the form of grids, patterns, lines, dots and the like.

In a particular aspect of the invention, the ultrasonic attachment means 800 can be configured to creating substantially permanent primary attachments 111 and substantially detachable or temporary secondary attachments 115 as show in the absorbent structure illustrated in FIG. 1. The attachment means provide an attachment and detachment system wherein the strength of the attachment means is great enough to adequately hold the carrier material 401 and the auxiliary material 501 together when the system is substantially dry and also when the absorbent structure is partially or fully wetted. In addition the attachment and detachment system is configured to be sufficiently low so as to not excessively constrict the swelling expansion of absorbent particulate polymer materials during the absorption of liquid. The strength of the attachment means is preferably less than the separating force imparted by the swelling of the high absorbency material when the absorbent particulate polymer material is exposed to liquids. In addition, the attachment system is preferably configured to release at an applied load which is less than the load needed to delaminate the attachment means without excessively tearing the material forming either or both of the carrier material 401 and/or auxiliary material 501 when such layers are wetted. The attachment system is preferably also configured to release at an applied load which is less than the load needed for the wetted absorbent material to burst through the material forming the absorbent structure. Typically, the applied load is a generally tensile load resulting from the pressure exerted by the expanding absorbent particulate polymer material when the particulate material absorbs liquid and swells. The appropriate attachment means are constructed and arranged to be sufficiently strong to withstand this pressure and substantially avoid bursting or tearing. Most preferably ultrasonic bonding systems are used to manufacture such composite structures which can for instance be supplied by Herrmann, from Germany.

The attachment means for securing together carrier material 401 and auxiliary material 501 may also be constructed to provide any other suitable connecting mechanism, such as adhesive bonds, thermal bonds, sonic bonds, stapling, stitching, or the like. The attachment means 800 can preferably be configured to provide operable pockets particulate material clusters 703 between the carrier layer 401 and auxiliary layer 501. Optionally, a perimeter means can be included in the process to obtain a mechanism for providing substantially continuous side attachment regions, and a selected pattern of intermittent, longitudinally-spaced, medial attachment regions. Suitable applicator devices are available from Nordson, a business having offices located at Norcross, Ga. Where the perimeter attachment means preferably comprises an adhesive applicator, the applicator may also be configured to apply the adhesive by employing various conventional techniques, such as printing, extrusion, spraying, or the like. In alternative configurations, the perimeter attaching means may be configured to provide other types of securing, such as sonic bonds, thermal bonds, stitching, sewing, etc.

The auxiliary material 501 can preferably be provided by covering means 500 and a guiding system 502 of transporting rollers and conveyers which are configured to deliver the auxiliary material 501 into a contacting relation with the composite structure 700 comprising a carrier material 401 and the printing pattern 320 of particulate material clusters 703.

Figure 13:
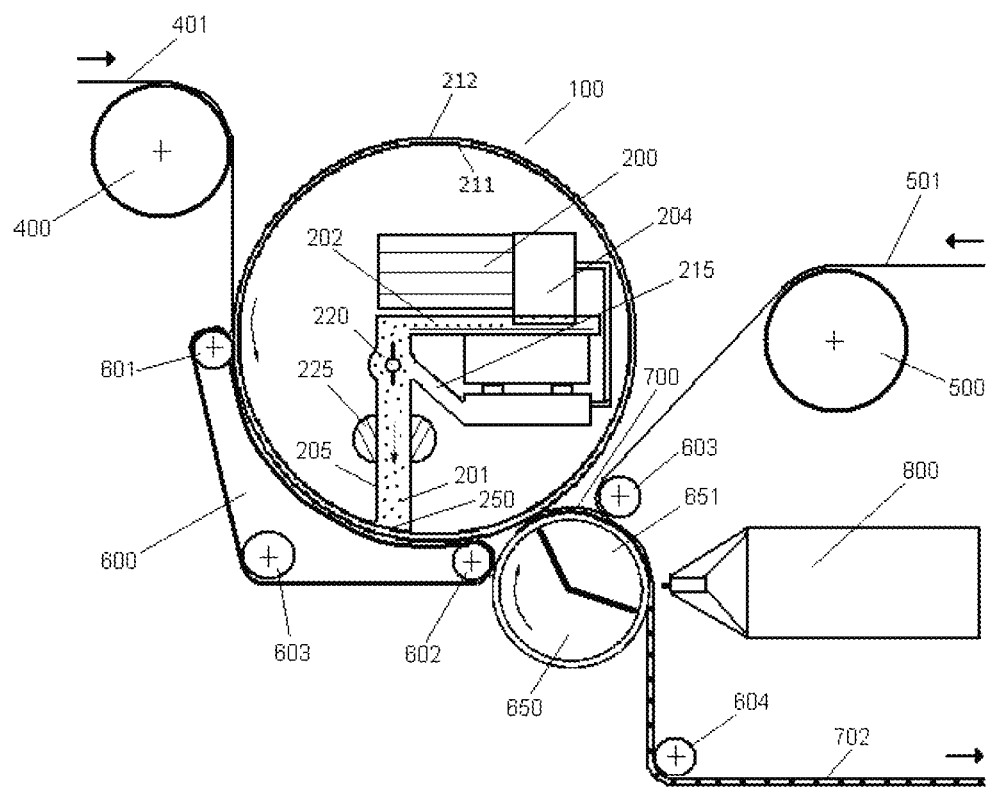
FIG. 13 provides schematic illustration of an apparatus for carrying out the invention according to an embodiment of the invention.

With reference to FIG. 13, a preferred embodiment of an apparatus and method according to this invention is illustrated, particularly suitable for manufacturing at very high speed super absorbent particle sheets as absorbent structures for absorbent articles such as a baby diaper. It includes a particle supply means 200 with feeding tube 205, recovery tube 215 and deflector 220, a clustering means 250 in the form of an essentially endless rotating drum 100, comprising perforations 304 in a desired perforation pattern 300. Below and in close proximity to the rotating drum 100, a moving carrier layer 401 is arranged onto an essentially endless support means 600, preferably moving at essentially the same speed as the rotating drum 100. Particles 201 falling out of the feeder means 200 in the drum 100 and onto the clustering means 250 into the perforations 304, thereby catching and gathering the desired amount of particulate material 201 for building up the particulate material clusters 703 which are to be deposited according to printing pattern 320. Via a takeover drum 650, with suction segment 651, the composite structure 700 of carrier layer 401 with printed pattern 320 is removed form the clustering means 250 and drum 100 before being covered by an auxiliary layer 501. A stripper roll can also be employed to help separate the composite structure 700 from the drum 100. An ultrasonic attachment system 800 is provided to bond and/or join the various layers of material to one another and preferably creating the predefined pockets with the particulate material clusters 703 by way of providing permanent and/or detachable bonds and/or joints within the inter-deposit zones 416 or inter-position zones, preferably throughout the absorbent polymer particulate material area. The positioning means, herein unitary with 651, stabilises, positions and/or repositions the particulate material 201 into its pocketing position 420 until it has been sandwiched and fixed by the ultrasonic sealing, creating the desired material 702. The takeover drum 650 preferably functions also as anvil for the ultrasonic tool. After the assembling operation has formed the desired material 702, the absorbent structure is preferably directed to other areas of the apparatus for further processing.

Creating constantly and quickly repeating pulses of particulate material 201 suspended in a conveyer means 225 such as air has been a long lasting desire for many applications, in particular for pulses which are well controlled both with regard to their shape, their frequency and the amount of material transferred during these pulses. A particular useful application is during the manufacture of disposable absorbent articles, such as feminine hygiene garments, baby diapers, baby pants and/or adult incontinence garments and the like, where the manufacturing aims at high production speed and low variability. This can be achieved by means of the deflector 220 which will interrupt the particle material stream by pushing the particulate material 201 into a recovery tube 215 and can thus create pulses of particulate material 201. The advantage is that one can thus choose not to print certain segments of the drum 100, i.e. leave certain areas of the perforation pattern 300 void of particle material. Also, the unprinted segments of the drum 100 can vary from one rotation of the drum to another, thereby saving enormously on the investment cost of providing different drums 100 with different perforation pattern 300, and on the maintenance and production cost of changing such different drums 100. As an example: with this solution, it is possible to manufacture composite structure 700 or absorbent for the use in absorbent articles such as diapers in all sizes, from the smallest one to fit a newborn baby unto the bigger ones for toddlers, on just one drum 100, which is not possible with conventional techniques known in the art and is highly appreciated and advantages.

Figure 12:
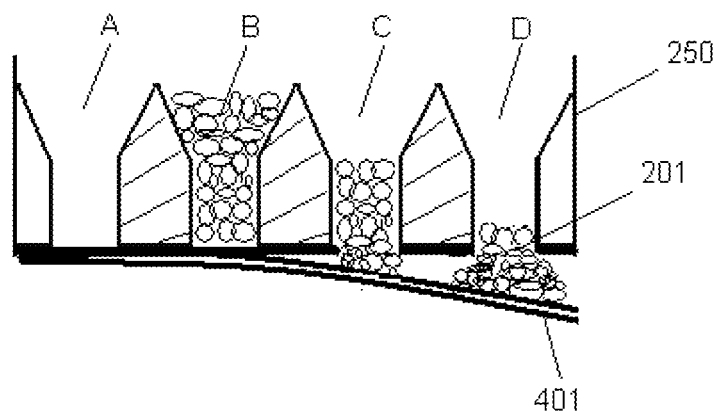
FIG. 12 provides schematic enlarged sectional view of a part of the equipment for the process as shown in FIG. 13.

FIG. 12 provides schematic enlarged sectional view of a part of the clustering means 250 depositing particulate material 201 via the perforations 304 onto their deposit region 415 according to a printing pattern 320 according to the process shown in FIG. 13. The perforations 304 are shown in four exemplary and non-limitative different states during the method according to the present invention; the first state "A" being the empty phase, just before loading of the perforations 304 or after having fully evacuated particulate material 201 there from; the second state "B" being the fully loaded state whereby the perforations 304 have collected particulate materials 201 so as to fill the perforation 304; the third state "C" being the start of the depositing process (partially) whereby the carrier layer 401 and the outer surface of the clustering means 250 are gradually moving away from each other such as is for instance the case when the substantially endless rotating drum 100 is departing from the carrier layer 401 thereby allowing partial evacuation of the particulate material 201; the last state "D" being the essentially full deposit of the particulate material cluster 703 onto the carrier layer 401 so as to, after full evacuation of the particulate material 201 onto the carrier layer 401, to return back to state "A", again allowing catching and collection of particulate materials 201 filling the void space for another particulate material cluster 703 depositing and printing pattern 320 process.

Figure 14:
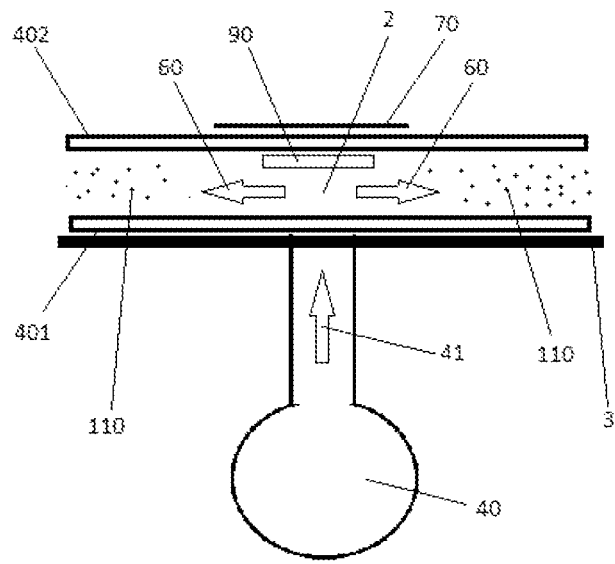
FIG. 14 provides a cross-sectional schematic illustration of an attachment process using airflows according to an embodiment of the invention.
Figure 15:
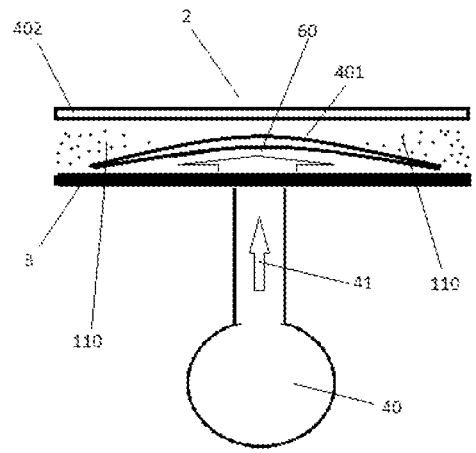
FIG. 15 provides a cross-sectional schematic illustration of an attachment process using airflows according to another embodiment of the invention.
Figure 16:
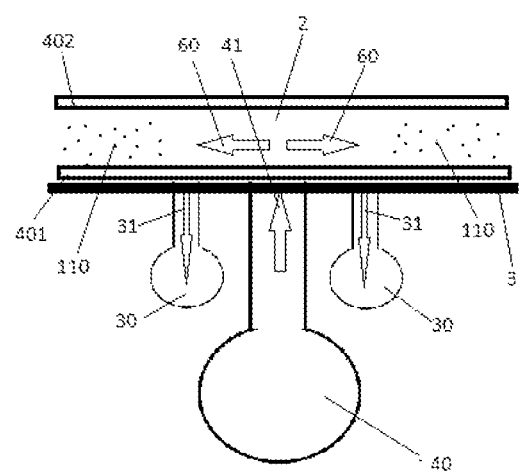
FIG. 16 provides a cross-sectional schematic illustration of an attachment process using airflows in a combination with blowing and suction holes according to another embodiment of the invention.
Figure 17:
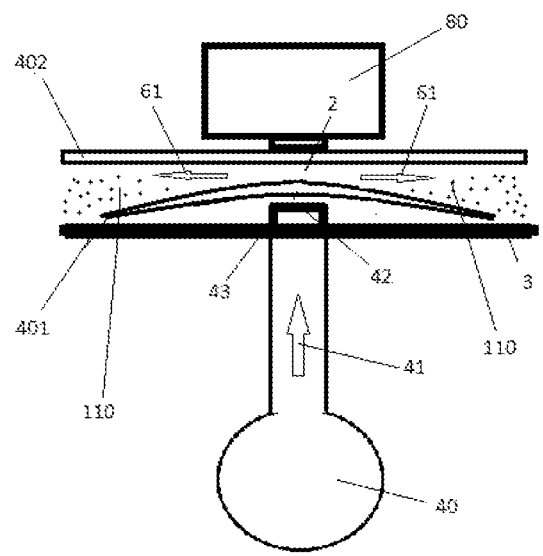
FIG. 17 provides a cross-sectional schematic illustration of an attachment process using airflows according to another embodiment of the invention.
Figure 18:
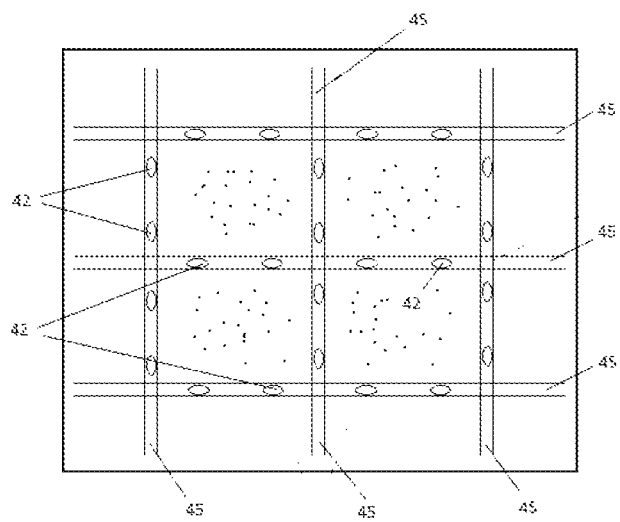
FIG. 18 provides a top view schematic illustration of an attachment process using airflows according to another embodiment of the invention showing blowing and/or suction holes.

With reference to FIG. 14, a carrier material 401 and an auxiliary material 402 will be attached in an attachment area 2, in the presence of an intermediate absorbent material 110. An attachment means 90 such as an adhesive is provided. A blowing hole 40 provides a blowing flow 41, creating resulting flows 60 which help to evacuate the intermediate absorbent material 110 from the attachment area 2. The carrier material 401 can be more or less air permeable. If the carrier material 401 has high air permeability, the airflow will more easily pass through the material and have a direct impact on the intermediate absorbent material 110 which will be evacuated more easily. In order to fully optimise the blowing flow 41, it is preferable though not necessary that the auxiliary material 402 is less or not air permeable. If the auxiliary material 402 is air permeable, it is possible to place and an additional material or mask 70 on top of the auxiliary material 402 so as to reduce or prevent air passing through the auxiliary material 402. The presence of an attachment means 90 such as a layer of adhesive will also form an extra barrier against air passing through the auxiliary material 402. With reference to FIG. 15, a carrier material 401 with lower air permeability has been used. Here the blowing flow 41 will result in a force directed upon the carrier material 401, relocating and lifting this carrier material 401 and thereby indirectly evacuating the intermediate absorbent material 110 from the attachment area 2. In most common materials, a combination of both effects, with some air passing through the carrier material 401 and directly evacuating the intermediate absorbent material 110, and some air remaining underneath the carrier material 401 and lifting this, will occur. With reference to FIG. 16, an auxiliary material 402 and a carrier material 401 will be attached in an attachment area 2, in the presence of an intermediate absorbent material 110. Suction holes 30 provide a suction flow 31 and blowing holes 40 provide a blowing flow 41. As a result, there is a resulting flow 60 which helps to evacuate intermediate absorbent material 110 from the attachment area 2. With reference to FIG. 17, an auxiliary material 402 and a carrier material 401 will be attached in an attachment area 2, in the presence of an intermediate absorbent material 110. Blowing holes 40 provide a blowing flow 41 via a blowing orifice 42 which is protruding from the tool surface 3. As a result, there is a resulting flow 61 which helps to evacuate the intermediate absorbent material 110 from the attachment area 2. The attachment means 90 can be a separate medium, such as for instance an adhesive (not shown). Alternatively, the protruding part 43 could act as an anvil for the sealing tool 80, which can for example be an ultrasonic hammer thus creating an ultrasonic attachment between auxiliary material 402 and carrier material 401. Alternatively, sealing tool 80 can be a heat sealing equipment, creating a heat sealed bond. The sealing tool 80 could then at least partly fulfill the function of blocking material 70 from FIG. 14. In FIG. 18, the protruding parts 43 of blowing holes 40 with blowing orifices 42 touch each other to form protruding arrays 45. In the midst of these arrays 45, there are evacuating channels 46 efficiently directing air flow and evacuating the intermediate material from attachment area 2.

It should be noted that at least part of the intermediate absorbent material 110 should be evacuated from the attachment area 2 prior to the attachment being made. This does not imply that auxiliary material 402 and carrier material 401 are both present when the intermediate absorbent material 110 is at least partly evacuated. On the contrary, one could easily provide the carrier material 401, evacuate part of the intermediate absorbent material 110 from the intended attachment area 2 and then, in a subsequent step, add the auxiliary material 402 and attach it to the carrier material 401.

Figure 19:
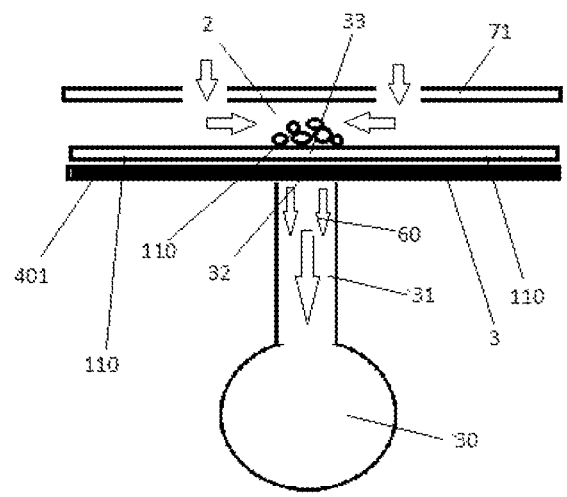
FIG. 19 provides a cross-sectional schematic illustration of another attachment process using airflows according to another embodiment of the invention.

FIG. 19 shows another preferred embodiment of this invention. An auxiliary material 402 and a carrier material 401 will be attached in an attachment area 2, in the presence of an intermediate absorbent material 110. The top material (not shown) will be added to the structure after at least part of the intermediate absorbent material 110 has been evacuated from the attachment area 2. A suction hole 30 provides a suction flow 31. An additional material or mask 71, having some openings which are not in line with the suction hole orifice 32 is provided. The combination of the suction force and the openings creates resulting flows 60 which help to evacuate the intermediate absorbent material 110 from the attachment area 2 by gathering it in an intermediate material landing zone 33.

Figure 20:
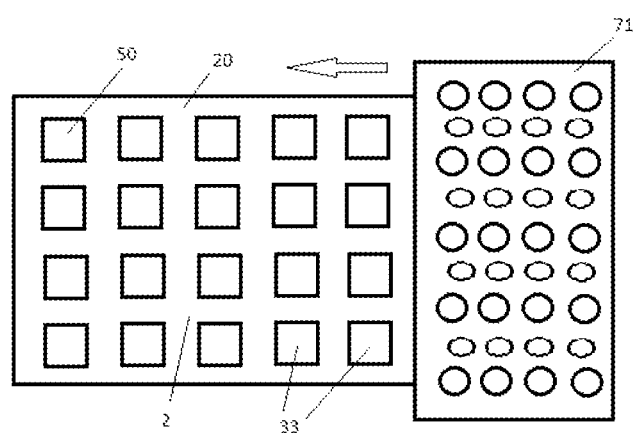
FIG. 20 provides a top view schematic illustration of an positioning means according to an embodiment of the invention using airflows in combination with a perforated mask.

For many applications, working with a suction segment can be more advantageous than working with a blowing segment as the latter often leads to a more turbulent airflow, resulting in less control of the evacuation of the intermediate material. However, it is clear that not all turbulence should be avoided for it can be used for the advantage of the process, as shown in FIG. 20. FIG. 20 shows a carrier material 401 is covered with an intermediate absorbent material 110. Underneath the carrier material 401 are suction holes with square suction hole orifices. By transporting the carrier material 401 and intermediate absorbent material 110 underneath a perforated mask 71, secondary airflows are created. These secondary airflows are somewhat turbulent in nature and guide the intermediate absorbent material 110 away from the attachment areas 2 where the intermediate absorbent material 110 finds few support towards the intermediate material landing zones 33 where there is a suction keeping it fixed.

Figure 21:
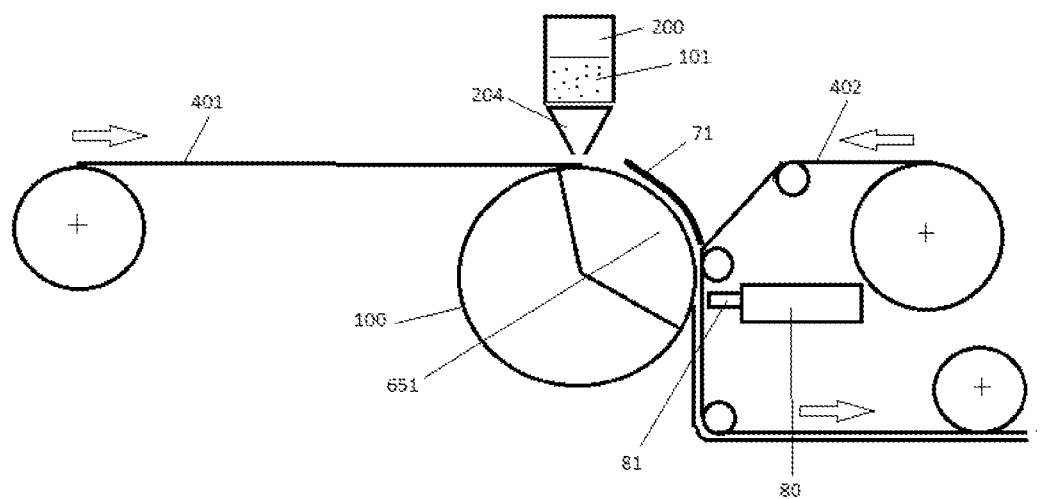
FIG. 21 provides a cross-sectional schematic illustration of a process according to an embodiment of the invention for manufacturing a composite structure of with enclosed particulate material by using airflows generated by means of additional positioning means.

FIG. 21 shows a process equipment for manufacturing an absorbent structure 14 with an intermediate absorbent material 110. A carrier material 410 is being provided and guided onto a rotating drum 200. Intermediate absorbent material 110 of a granular nature is provided out of a particulate material supplying means 200 via a dosing system 204. Within a section segment 651 of the drum 100, an under-pressure or vacuum is created via perforations with orifices 32. Above the drum, there is a mask 71 with openings, creating airflows which will guide the intermediate absorbent material 110 onto the positioning pattern 420 and away from the inter-positioning zones. An auxiliary layer 402 is added and it is attached to the carrier material 401 20 by means of an ultrasonic equipment 81 with a hammer 80. The drum 100 acts as anvil for the ultrasonic sealing. The resulting absorbent structure 14 is guided away from the equipment.

The process for producing preferred absorbent structures in accordance with the present invention comprises the following steps: A carrier layer 10 is provided onto which absorbent intermediate material 50 is disposed by methods known in the art. To deposit the absorbent material 50, vacuum, gravity, airflow or other forces can be used. Then an auxiliary layer 20 is provided, covering the absorbent material 50, and primary bonding regions 2 and secondary bonding regions 4 are being provided. In case one would like to use adhesives or chemical binders, then it might be useful to attach these to the carrier layer 10 and/or auxiliary layer 20 prior to bringing the sandwich structure together. In case one opts for thermo-sealed bonding areas, then the thermo-sealing can be applied after the sandwich structure components have been brought together. It is of course also possible to combine both techniques in the same absorbent structure.

The sizes and shapes of the holes, the pressure differences and other parameters described in this invention may vary and depend on the application. However, the person skilled in the art will be able to determine the settings which are most suitable for his application. For example, for absorbent article applications in personal hygiene, such as in the manufacturing sheet with absorbent polymer materials, the absorbent structure 14 can be manufactured according to settings as described above in relation to FIGS. 20 and 21. The perforations in the mask can be manufactured having a diameter between 0.5 mm and 10 mm, more preferably between 2 and 7 mm, and most preferably between 3 and 5 mm. The distance to the rotating drum is preferably smaller than 25 mm, more preferably smaller than 15 mm and most preferably around 5 mm. The vacuum or under pressure in the suction segment 651 should preferably be larger in magnitude than −1.0 kPa, more preferably larger in magnitude than −7.5 kPa and most preferably larger in magnitude than −15 kPa. The auxiliary and carrier materials can be chosen from a wide range of materials. It has been found that using polypropylene spunbonded nonwoven materials with a weight between 8 and 20 grams per sqm give excellent results.

Figure 22:
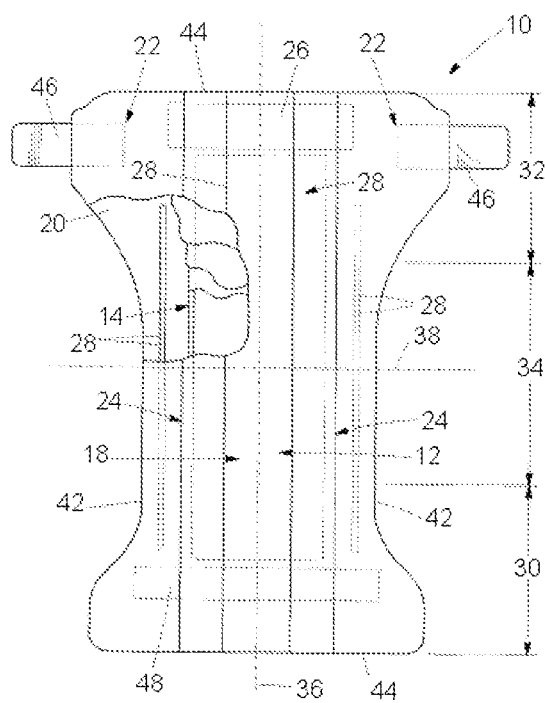
FIG. 22 provides a top plan view of a diaper as a preferred embodiment of an absorbent article comprising an absorbent

FIG. 22 is a top plan view of a diaper 10 as a preferred embodiment of an absorbent article including an absorbent structure made according to the present invention. It should be understood, however, that the present invention is also applicable to other absorbent articles such as feminine hygiene garments, baby pants, adult incontinent garments and the like.

The absorbent article is shown in its flat out, un-contracted state with the wearer side facing the viewer. Portions of the absorbent article are cut away to more clearly show the underlying structure of the diaper 10 including the absorbent elements and absorbent components. The chassis 12 of the diaper 10 in FIG. 22 comprises the main body of the diaper 10. The chassis 12 comprises an outer covering including a liquid pervious top sheet 18 and/or a liquid impervious back sheet 20. The chassis 12 may include a portion of an absorbent structure 14 encased between the top sheet 18 and the back sheet 20. The chassis 12 may also include most or all of the absorbent structure 14 encased between the top sheet 18 and the back sheet 20. The chassis 12 preferably further includes side panels or ears 22, elasticized leg cuffs 24 and elastic waist features 26, the leg cuffs 24 and the elastic waist feature 26 each typically comprise elastic members 28. One end portion of the diaper 10 is configured as a front waist region 30 of the diaper 10. The opposite end portion is configured as a back waist region 32 of the diaper 10. An intermediate portion of the diaper 10 is configured as a crotch region 34, which extends longitudinally between the first and second waist regions 30 and 32. The waist regions 30 and 32 may include elastic elements such that they gather about the waist of the wearer to provide improved fit and containment (e.g. elastic waist feature 26). The crotch region 34 is that portion of the diaper 10 which, when the diaper 10 is worn, is generally positioned between the wearers legs. The diaper 10 is depicted with its longitudinal axis 36 and its transverse axis 38. The periphery of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper. The chassis 12 also comprises a fastening system, which may include at least one fastening or securing member 46 and at least one landing zone 48. The various components within the diaper 10 may be bound, joined or secured by any method know in the art, for example by adhesives in uniform continuous layers, patterned layers or arrays of separate lines, spirals or spots. The top sheet 18, the back sheet 20, the absorbent structure 14 and other components may be assembled in a variety of well-known configurations and are well known in the art.

The back sheet 20 covers the absorbent structure 14 and preferably extends beyond the absorbent structure 14 toward the longitudinal edges 42 and end edges 44 of the diaper 10 and may be joined with the top sheet 18. The back sheet 20 prevents the bodily exudates absorbed by the absorbent structure 14 and contained within the diaper 10 from soiling other external articles that may contact the wearer, such as bed sheets and undergarments. In preferred embodiments, the back sheet 20 is substantially impervious to bodily exudates and comprises a laminate of a non-woven and a thin plastic film such as a thermoplastic film. The back sheet 20 may comprise breathable materials that permit vapour to escape from the diaper 10 while still preventing bodily exudates from passing through the back sheet 20. It may be semi-rigid, non-elastic and can be made fully or partially elasticized and include backing. The back sheets 20 may be assembled in a variety of well-known configurations and are well known in the art.

The diaper 10 comprises a top sheet 18 that is preferably soft, compliant, exhibits good strikethroughs and has a reduced tendency to rewet from the liquid absorbent material. The top sheet 18 is placed in close proximity to the skin of the wearer when the diaper 10 is worn. In this way, such top sheet 18 permits bodily exudates to rapidly penetrate it so as to flow toward the absorbent structure 14 more quickly, but preferably not allowing such bodily exudates to flow back through the top sheet 18. The top sheet 18 may be constructed from any one of a wide range of liquid and vapour permeable, preferably hydrophilic, materials. The upper and lower surface of the top sheet 18 may be treated differently and may for instance include a surfactant on the upper surface so as to facilitate liquid transfer there through, especially at a central zone or area of the top sheet 18 located over the absorbent structure 10, and for instance include a hydrophobic agent on the lower surface to minimize the liquid contained within the absorbent core from contact wetting the top sheet 18 thereby reducing rewet values. The top sheet 18 may also be coated with a substance having rash preventing or rash reducing properties (e.g. aloe vera). The top sheet 18 covers substantially the entire wearer facing area of the diaper 10, including substantially all of the front waist region 30, back waist region 32, and crotch region 34. Further, the side panels 22 and/or waist feature layers of the inner region may be formed from the same single top sheet material and, thus, may be referred to as being unitary with the top sheet 18 in forming longitudinal and lateral extensions of the top sheet 18 material. Alternatively, the top sheet 18 may be formed from multiple different materials which vary across the width of the top sheet 18. Such a multiple piece design allows for creation of preferred properties and different zones of the top sheet 18. The top sheet 18 be semi-rigid, non-elastic and can be made fully or partially elasticized. The top sheet 18 may be assembled in a variety of well-known configurations and are well known in the art.

The absorbent structure 14 in FIG. 22 generally is disposed between the top sheet 18 and the back sheet 20. The absorbent structure 14 may comprise any absorbent material 110 that is generally compressible, conformable, non-irritating to the wearer's skin, and capable of absorbing and retaining bodily exudates. The absorbent structure 14 may comprise a wide variety of liquid absorbent materials 110 commonly used in absorbent articles such as fluff pulp, which is generally referred to as airlaid. Examples of other suitable absorbent materials include creped cellulose wadding; melt blown polymers; chemically stiffened, modified or cross-linked cellulosic fibres; tissue, including tissue wraps and tissue laminates; absorbent foams; absorbent sponges; absorbent polymer materials; absorbent gelling materials; or any other known absorbent materials or combinations of materials. The absorbent structure 14 may further comprise minor amounts (typically less than 10%) of non-liquid absorbent materials, such as adhesives, binders, plastics, waxes, oils and the like. The absorbent structure 14 according to various embodiments of the invention may be configured to extend substantially the full length and/or width of the diaper 10. However, alternatively the absorbent structure 14 according to the invention is not coextensive with the entire diaper 10 and is limited to certain regions of the diaper 10 such as for instance the crotch region 34. In various embodiments, the absorbent structure 14 extends to the edges of the diaper 10 and the absorbent material 110 is concentrated in the crotch region 34 or another target zone of the diaper 10. In still another embodiment, the particles can be a combination of absorbent material 110, preferably comprising absorbent polymer material, and skin care particles such as ion exchange resins, deodorant, anti-microbial agents, binder particles, or other beneficial particles.

The diaper 10 may also utilize a pair of containment walls or cuffs 24. Each cuff 24 is a longitudinally extending wall structure preferably positioned on each side of the absorbent structure 14 and spaced laterally from the longitudinal axis 36. The longitudinal ends of the cuffs 24 may be attached or joined, for example, to the top sheet 18 in the front and rear waist regions 30 and 32. Preferably, the ends of the cuffs 24 are tacked down inwardly and attached, for example, by adhesive or sonic bonding to the lower structure. Such a construction effectively biases the cuffs 24 inwardly and is generally considered to cause the cuffs 24 to exhibit improved leakage prevention properties. Preferably, the cuffs 24 are equipped with elastic members 28, which extend along a substantial length of the cuffs 24. In a common application, the elastic members 28 are placed within the cuffs 24, preferably at the top of the cuff 24 while in a stretched condition and then glued or sonic bonded to the cuff 24 at least at their ends. When released or otherwise allowed relaxing, the elastic members 28 retract inwardly. When the diaper 10 is worn, the elastic members 28 function to contract the cuffs 24 about the buttocks and the thighs of the wearer in a manner, which forms a seals between the diaper 10, the buttocks and the thighs. The cuffs 24 may be assembled in a variety of well-known configurations and are well known in the art.

The diaper 10 may also employ additional layers known in the art including an acquisition layer or surge layer, preferably situated between the top sheet and the absorbent core and highloft and/or coverstock layers. This serves to slow down the flow so that the liquid has adequate time to be absorbed by the absorbent core.

In order to keep the diaper 10 in place about the wearer, preferably at least a portion of the back waist region 32 is attached by fastening or securing members 46 to at least a portion of the front waist region 30, preferably to form leg openings and an absorbent article waist. Fastening or securing members 46 carry the tensile load around the absorbent article waist and compliment the elastic members 28 by providing a quasi-seal between the wearer, the elastic waist feature 26 and cuffs 24, so that bodily exudates are contained within the diaper 10 which are then absorbed. In other words, so that it does not leak through gaps between the wearer and the edge of the diaper 10. The fastening or securing members 46 may for instance be adhesive, mechanical fasteners, hook and loop features, conceivable strings and/or combinations thereof, i.e., anything that will secure one end of the diaper 10 to the longitudinally opposite end of the diaper 10. The fastening or securing members 46 may also be co-adhesive such that they adhere to each other but not other materials. The fastening or securing members 46 and any component thereof may include any material suitable for such a use, including but not limited to plastics, films, foams, non-woven webs, woven webs, paper, laminates, fibre reinforced plastics and the like, or combinations thereof. It may be preferable that the materials making up the fastening or securing members 46 are flexible, extensible and/or elastic, allowing them to better conform to the shape and movements of the body and thus, reduces the likelihood that the fastening system will irritate or injure the wearer's skin. Preferably, the diaper 10 is affixed to the wearer by tape fasteners which are permanently affixed to the back sheet 20. Tape fasteners are contacted with the transversely opposite side panel or ears 22 attached or joined and extending from the back sheet 20, where they remain affixed due to the binding compound applied to the fasteners. Alternatively, the absorbent article may be pants and the like. In this configuration, the absorbent article may or may not have tape fasteners. Specific disposability tapes may however also be provided on such absorbent articles. All fastening and securing elements 46 may be assembled in a variety of well-known configurations and are well known in the art.

The waist regions 30 and 32 each comprise a central region and a pair of side panels or ears 22 which typically comprise the outer lateral portions of the waist regions. These side panels 22 may be unitary with the chassis 12 and/or back sheet 20 or may be attached or joined thereto by any means know in the art. In a preferred embodiment of the present invention, the side panels 22 positioned in the back waist region 32 are flexible, extensible and/or elastic in at least the lateral direction (i.e., elasticized side panels), in another embodiment the side panels 22 are non-elastic, semi-rigid, rigid and/or stiff. This variety of side panels 22 are well known.

Furthermore waistbands 26 employing elastic members can be positioned along the transverse portion of the diaper 10 so that when worn, the waistbands 26 are positioned along the waist of the wearer. Generally, the waistband 26 preferably creates a seal against the waist so that bodily exudates do not leak from the regions between the elastic waistband 26 and the waist of the wearer. Although the bodily exudates are primarily absorbed by the absorbent materials within the diaper 10, the seal is important considering the assault of liquid by the wearer may overwhelm the absorption rate capacity of the absorbent structure 14. Hence, the waistbands 26 contain the liquid while it is being absorbed, they are well known in the art. The absorbent article such as a diaper 10 may also include such other features, components and elements as are known in the art including front and rear ear panels, waist cap features, elastics and the like to provide better fit, containment and aesthetic characteristics. These features may be assembled in a variety of well-known configurations and are well known in the art.

What is claimed is:

1. A method for producing a composite structure comprising a pattern of absorbent particulate polymer material, the method comprising the steps of:
   a—providing at least one essentially endless layer as a carrier layer;
   b—providing an essentially endless support means for the carrier layer;
   c—positioning the carrier layer over the support means; whereby the carrier layer is in contact with a contact surface of the support means, the speed of the carrier layer, contact surface of
   the carrier support means and a clustering means being essentially the same;
   d—providing a particulate material stream from a particle material supply means;
   e—directing the particulate material through perforations of a clustering means;
   g—combining the carrier layer and an auxiliary layer with the particulate material sandwiched there between;
   characterized in that,
   h—the clustering means guide the particulate material towards the carrier layer thereby creating a printing pattern of particulate material;

I—the printing pattern being positioned by positioning means thereby forming a pocket pattern of particulate material on the carrier material;

j—and in that the positioning means substantially evacuate by an airflow particulate material from inter-pocket pattern zones into the pocket pattern before joining the carrier layer and auxiliary layer to form a pattern of particulate material;

wherein the clustering means is a rotating drum, and
wherein the positioning means is mounted on or is unitary with the support means.

2. A method according to claim 1, characterized in that the method comprises the step of removing from the clustering means particulate material which has not been caught by the perforations of the clustering means.

3. A method according to claim 1, characterized in that the method comprises evacuating substantially all particulate materials via bottom openings of the clustering means towards the carrier layer.

4. A method according to claim 1, characterized in that the method comprises moving the carrier layer and interrupting the particle material stream to create intervals on the carrier layer where no particulate materials have been deposited.

5. A method according to claim 1, characterized in that at least one carrier layer and/or auxiliary layer comprises liquid permeable non-woven, paper or tissue.

6. A method according to claim 1, characterized in that the pocket pattern does not correspond to the printing pattern and in that the airflow of the positioning means is applied to cluster the particulate material according to the printing pattern into the pocket pattern which is more heterogeneous than the printing pattern.

* * * * *